US012763176B2

(12) United States Patent
Makino

(10) Patent No.: US 12,763,176 B2
(45) Date of Patent: Oct. 13, 2026

(54) VIEWING PROCEDURE MANAGEMENT SYSTEM AND VIEWING PROCEDURE MANAGEMENT METHOD

(71) Applicant: ID Holdings Corporation, Tokyo (JP)

(72) Inventor: Takeaki Makino, Tokyo (JP)

(73) Assignee: ID Holdings Corporation, Tokyo (JP)

( * ) Notice: Subject to any disclaimer, the term of this patent is extended or adjusted under 35 U.S.C. 154(b) by 50 days.

(21) Appl. No.: 18/612,212

(22) Filed: Mar. 21, 2024

(65) Prior Publication Data

US 2025/0299789 A1 Sep. 25, 2025

(51) Int. Cl.

| | |
|---|---|
| ***G06F 17/00*** | (2019.01) |
| ***G06F 21/31*** | (2013.01) |
| ***G06F 21/62*** | (2013.01) |
| ***G16H 10/60*** | (2018.01) |

(52) U.S. Cl.

CPC ............. *G16H 10/60* (2018.01); *G06F 21/31* (2013.01); *G06F 21/6245* (2013.01)

(58) Field of Classification Search

CPC ...... G16H 10/60; G06F 21/31; G06F 21/6245

See application file for complete search history.

(56) References Cited

U.S. PATENT DOCUMENTS

| | | | | |
|---|---|---|---|---|
| 7,039,810 | B1 * | 5/2006 | Nichols | G16H 40/40 713/193 |
| 9,202,084 | B2 * | 12/2015 | Moore | G06F 16/9535 |
| 11,406,265 | B2 * | 8/2022 | Dirghangi | G16H 40/63 |
| 11,705,228 | B2 * | 7/2023 | Ishikawa | G16H 40/20 705/3 |
| 2019/0027237 | A1 * | 1/2019 | McFarlane | G16H 80/00 |

(Continued)

FOREIGN PATENT DOCUMENTS

| | | |
|---|---|---|
| JP | 6801922 B2 | 12/2020 |
| JP | 6936763 B | 9/2021 |

OTHER PUBLICATIONS

Hongjiao Wu, Ashutosh Dhar Dwivedi, and Gautam Srivastava. 2021. Security and Privacy of Patient Information in Medical Systems Based on Blockchain Technology. ACM Trans. Multimedia Comput. Commun. Appl. 17, 2s, Article 60 (Jun. 2021), 17 pages. <https://doi.org/10.1145/3408321>, June (Year: 2021).*

(Continued)

*Primary Examiner* — Greta L Robinson

(74) *Attorney, Agent, or Firm* — Nakanishi IP Associates, LLC

(57) ABSTRACT

For sufficient use of patient examination data generated at multiple medical institutions, a request node (2*a*) in multiple patient examination nodes (2) generates and transmits a request message requesting viewing of target examination data to the generation node (2*b*). The generation node authenticates a signature of a target patient received together with the request message, generates a permission message requesting setting of a viewing right of the target examination data to the request node, and transmits the message to an authentication node (3). The signature of the target patient and a signature of the generation node are included in or attached to the permission message. The authentication node generates, after receiving the permission message, a data block to set the viewing right of the target examination data to the request node and transmits the data block to the patient examination nodes for storage in a blockchain format.

6 Claims, 14 Drawing Sheets

(56) References Cited

U.S. PATENT DOCUMENTS

2023/0170079 A1* 6/2023 Gnanasambandam ...................... G16H 50/70 705/2
2023/0360779 A1* 11/2023 Gnanasambandam ...................... G06Q 20/3678

OTHER PUBLICATIONS

Shuang Liu et al., A Consortium Medical Blockchain Data Storage and Sharing Model Based on IPFS. In 2021 The 4th International Conference on Computers and Management and Business (ICCMB 2021), ACM, 7 pages, Association for Computing Machinery, <https://doi.org/10.1145/3450588/3450944>, January (Year: 2021).*
Mayumi Maeda, Legal Aspects of Medical Records: Review of Judicial Precedents. Journal of the Japanese Society for Medical Education, Jun. 2005, 36(3), 153-157 (5 pages).

* cited by examiner

FIG. 13
I, John Doe, approve the viewing of my medical examination records created between Month A, 20XX and Month B, 20YY and stored at AAA Department, BBB Hospital, by doctors in CCC Department, DDD Hospital.
Date of approval: YYYY/MM/DD
Viewing expiration date: YYYY/MM/DD
FIG. 14
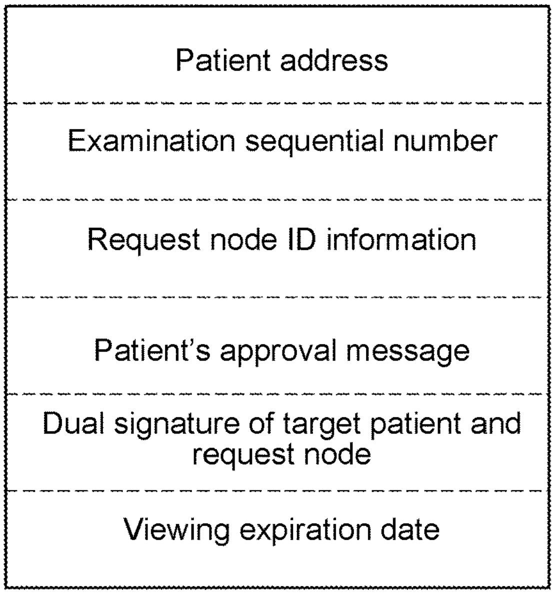
FIG. 15
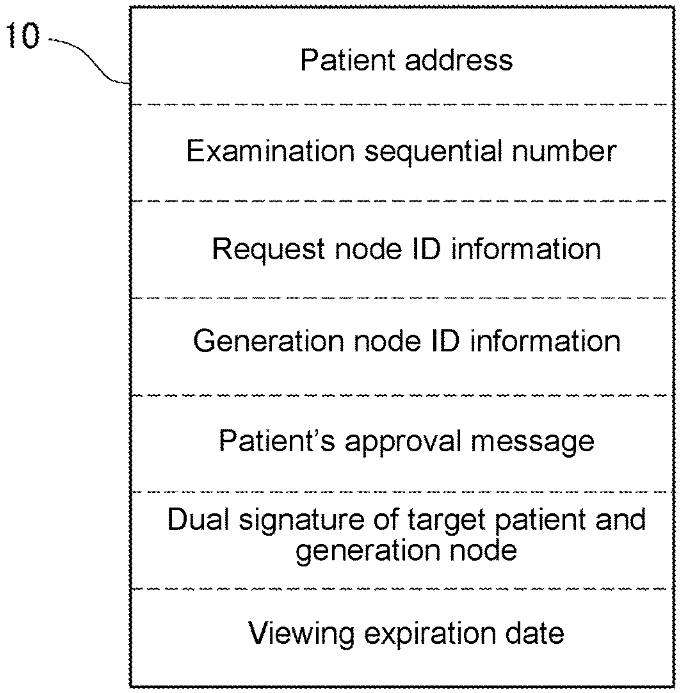

VIEWING PROCEDURE MANAGEMENT SYSTEM AND VIEWING PROCEDURE MANAGEMENT METHOD

BACKGROUND OF INVENTION

Field of the Invention

The present invention relates to a technique for managing a viewing procedure taken by multiple patient examination nodes connected through a communication line to view patient examination data generated based on examinations of patients and held by the patient examination nodes.

Background Art

When examining a patient, a doctor may refer to a patient examination record of the patient (e.g., test images, test values, and observations by another doctor) held at another medical institution. In this case, the doctor requests the other medical institution at which the patient has previously received an examination to provide the patient examination record.

However, the procedure of the medical institution may not be as simple as to provide the patient examination record as requested, because the patient examination is more than a record of test results (e.g., test images and test values) but reflects, for example, accumulated clinical experience and medical knowledge of the doctor and treatment policy based on such experience and knowledge. The patient examination record may contain information having the authorship of the doctor. Additionally, the patient examination record may include highly sensitive personal information about the patient for which any mishandling may violate the patient's privacy right. The medical institution may possibly be involved in an unexpected legal action associated if the institution provides such a patient examination record as requested. Under these circumstances, clinical sites have reported their hesitation to actively share patient examination records among multiple medical institutions (Non-Patent Literature 1).

In response to this, a technique has been developed (Patent Literature 1) for storing patient examination records generated by multiple medical institutions into a patient examination record database, storing record identification information for referring to the patient examination records into a blockchain database, and storing the record identification information into a registration information database in a manner associated with patient identification information for identifying patients. This technique allows a third party such as an insurance company to refer to the patient examination records over a long period.

Another technique has been developed (Patent Literature 2) for storing patient prescription data into a blockchain database, permitting, with an operation by a patient on a terminal, a doctor to access the database to issue a prescription or a pharmacist to access the database to refer to a prescription, and then removing the access permission from the doctor or pharmacist once an accounting operation for the prescription is complete.

CITATION LIST

Patent Literature

Patent Literature 1: Japanese Patent No. 6801922
Patent Literature 2: Japanese Patent No. 6936763

Non-Patent Literature 1: Mayumi Maeda, Legal Aspects of Medical Records: Review of Judicial Precedents. Journal of the Japanese Society for Medical Education, June 2005, 36(3), 153-157.

SUMMARY OF INVENTION

However, the above known techniques may not allow sufficient use of patient examination records stored at multiple medical institutions. For example, the technique described in Patent Literature 1 above allows a past patient examination record to be obtained easily by an insurance company or another party but cannot prove that the patient examination record has been obtained or provided with the consent of the patient or the doctor who created the patient examination record. Thus, a party who has obtained or provided such a patient examination record may possibly be involved in an unexpected legal action. The technique described in Patent Literature 2 described above can prove that a prescription has been provided with the consent of the patient when a medicine is prepared based on the prescription, but cannot prove that a patient examination record has been provided with the consent of the doctor or patient when the patient examination record is received. Thus, a party who has obtained or provided such a prescription or a patient examination record may possibly be involved in an unexpected legal action.

To solve the issue described above with the known techniques, one or more aspects of the present invention are directed to a patient examination record management system for easily proving, later, that a patient examination record held at a medical institution is obtained or provided with the consent of a patient and a doctor, allowing a patient examination record to be obtained or provided with an easy procedure, and thus allowing sufficient use of a patient examination record.

A viewing procedure management system according to one or more aspects of the present invention uses the technique described below. The viewing procedure management system for managing a procedure for patient examination data to be viewable by a plurality of patient examination nodes includes the plurality of patient examination nodes, and an authentication node. Each of the plurality of patient examination node generates patient examination data based on an examination of a patient and stores a plurality of data blocks in a blockchain format. The authentication node generates the plurality of data blocks to be stored into the plurality of patient examination nodes. The plurality of patient examination nodes and the authentication node are connected through a communication line. Each of the plurality of patient examination nodes includes a data block storage that stores the plurality of data blocks in the blockchain format, and an examination data output unit that outputs the generated patient examination data to a database connected to the patient examination node. The plurality of patient examination nodes include a patient examination node being a request node that requests viewing of the patient examination data generated by another patient examination node of the plurality of patient examination nodes and a patient examination node being a generation node that generates target examination data being the patient examination data requested by the request node for viewing. The request node includes a request message transmitter that generates and transmits a request message requesting viewing of the target examination data to the generation node. The request message is a message including predetermined signature data with a signature of a target patient relating to the target examination data or a message to which the signature data with the signature of the target patient relating to the target examination data is attached. The generation node includes a patient signature authenticator, an identification information obtainer, a permission message generator, and a permission message transmitter. The patient signature authenticator authenticates, when receiving the request message, the signature of the target patient relating to the signature data received together with the request message. The identification information obtainer obtains, when the signature of the target patient is authenticated, examination data identification information identifying the target examination data and request node identification information identifying the request node. The permission message generator generates a permission message requesting setting of a viewing right for the request node to view the target examination data. The permission message includes the examination data identification information and the request node identification information. The permission message is a message including the signature data with the signature of the target patient and signature data with a signature of the generation node or a message to which the signature data with the signature of the target patient and the signature data with the signature of the generation node are attached. The permission message transmitter transmits the permission message to the authentication node. The authentication node includes a data block generator and a data block transmitter. After the authentication node receives the permission message, the data block generator generates a data block. The data block includes the signature of the target patient and the signature of the generation node to set the viewing right of the target examination data to the request node. The data block transmitter transmits the generated data block to the plurality of patient examination nodes.

A viewing procedure management method according to one or more aspects of the present invention corresponding to the viewing procedure management system according to the above aspect of the present invention uses the technique described below. A viewing procedure management method for managing a procedure for patient examination data to be viewable by a plurality of patient examination nodes is implementable with the plurality of patient examination nodes each to generate patient examination data based on an examination of a patient and store a plurality of data blocks in a blockchain format and with an authentication node to generate the plurality of data blocks to be output to the plurality of patient examination nodes. The plurality of patient examination nodes and the authentication node are connected through a communication line to communicate with one another with a network. The method includes generating and transmitting, with a request node being a patient examination node of the plurality of patient examination nodes requesting viewing of the patient examination data generated by another patient examination node of the plurality of patient examination nodes, a request message to a generation node being a patient examination node of the plurality of patient examination nodes generating target examination data being the patient examination data requested by the request node for viewing, the request message requesting viewing of the target examination data. The request message is a message including predetermined signature data with a signature of a target patient relating to the target examination data or a message to which the signature data with the signature of the target patient relating to the target examination data is attached. The method includes authenticating, with the generation node, the signature of the target patient relating to the signature data received together with the request message. The method includes obtaining, with the generation node, when the signature of the target patient is authenticated, examination data identification information identifying the target examination data and request node identification information identifying the request node. The method includes generating, with the generation node, a permission message requesting setting of a viewing right for the request node to view the target examination data and transmitting, with the generation node, the permission message to the authentication node. The permission message includes the examination data identification information and the request node identification information. The permission message is a message including the signature data with the signature of the target patient and signature data with a signature of the generation node or a message to which the signature data with the signature of the target patient and the signature data with the signature of the generation node are attached. The method includes generating, with the authentication node, after receiving the permission message with the authentication node, a data block and transmitting, with the authentication node, the data block to the plurality of patient examination nodes. The data block includes the signature of the target patient and the signature of the generation node to set the viewing right of the target examination data to the request node.

In the viewing procedure management system and with the viewing procedure management method described above, the request node requests viewing of patient examination data generated by another patient examination node by generating a request message requesting viewing of the target examination data and transmits the message to the generation node. The generation node determines that consent has been obtained from the target patient based on the signature of the target patient transmitted together with the request message. The generation node generates a permission message requesting setting of a viewing right of the target examination data to the request node, and transmits the message to the authentication node. After receiving the permission message, the authentication node generates a data block including the signature of the target patient and the signature of the generation node transmitted together with the permission message for setting the viewing right of the target examination data to the request node, and transmits the data block to the multiple patient examination nodes including the request node. The patient examination nodes each store the data block transmitted from the authentication node in the blockchain format.

This allows the viewing right of the target examination data to be easily determined to have been set to the request node with the consent of the target patient and the generation node by examining the block data stored in the multiple patient examination nodes. The request node can thus easily prove, later, its viewing of the target examination data with the consent of the target patient and the generation node. The generation node can easily prove, later, allowing viewing of the target examination data by the request node with the consent of the target patient. Thus, viewing of patient examination data generated by another patient examination node or allowing viewing of patient examination data by another patient examination node does not cause an unexpected legal action, thus allowing sufficient use of a patient examination node.

In the above viewing procedure management system according to the above aspect of the present invention, the authentication node may authenticate, after receiving the permission message including the signature of the target patient and the signature of the generation node, at least the signature of the generation node based on the signature of the generation node. When the signature of the generation node is authenticated, the authentication node may generate the data block described and transmit the data block to the multiple patient examination nodes. When authenticating the signature of the generation node, the authentication node may also authenticate the signature of the target patient.

When the signature of the generation node is successfully authenticated, it shows that the consent has been obtained from the generation node. Because a data block is generated only after the signature of the generation node is successfully authenticated, this prevents unauthorized generation of a data block (in other words, a data block that cannot prove the consent of the generation node later) as well as its storage in the blockchain format. The signature of the target patient may also be authenticated, and a data block may be generated only after the signature of the target patient is successfully authenticated. This can prevent generation of a data block that cannot prove the consent of the target patient later as well as storage of such a data block in the blockchain format.

In the viewing procedure management system according to the above aspect of the present invention, signature data with the signature of the target patient and signature data with the signature of the generation node included in or attached to the permission message may be a single piece of signature data with signatures of the target patient and the generation node, rather than two separate pieces of signature data with the signatures.

In this case, the signature data with the signature of the target patient and the signature data with the signature of the generation node can be integrated into the single piece of signature data, decreasing the volume of data transmitted from the generation node to the authentication node and allowing rapid transmission and decreasing the burden on the network.

In the viewing procedure management system according to the above aspect of the present invention, the data block generator in the authentication node may generate a data block including a viewing expiration date of the target examination data.

The target patient or the generation node that has consented to viewing of the target examination data may not have consented to such viewing for an unlimited period of time. The above structure can prevent the target examination data from being viewed for an unlimited period of time.

The viewing procedure management system according to the above aspect of the present invention may set the viewing expiration date in the manner described below. The request node first obtains the viewing expiration date from the target patient and transmits the request message to the generation node together with the viewing expiration date. The generation node generates and transmits the permission message including the received viewing expiration date to the authentication node. The authentication node then reads the viewing expiration date from the permission message and sets the viewing expiration date to the data block.

This prevents viewing of the target examination data exceeding the viewing expiration date to which the target patient consents.

BRIEF DESCRIPTION OF THE DRAWINGS

FIG. 13 is an example of a patient's approval message to be signed at the patient terminal 6.

FIG. 14 is a diagram describing multiple pieces of information included in a request message generated by the request node 2*a*.

FIG. 15 is a diagram describing multiple pieces of information included in a permission message generated by the generation node 2*b*.

DETAILED DESCRIPTION

A. Overview of Viewing Procedure Management System 1

Figure 1:
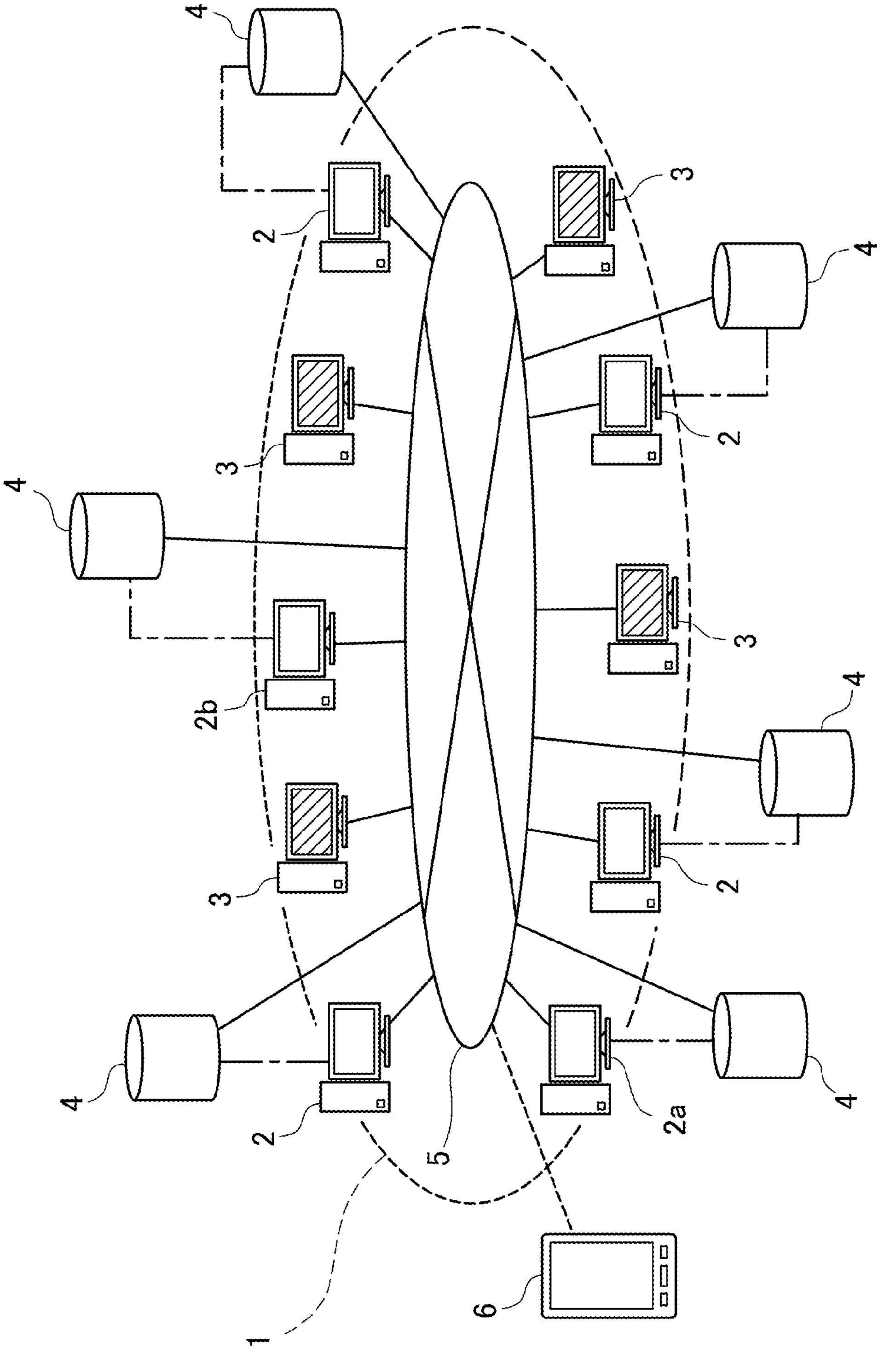
FIG. 1 is a schematic diagram of a viewing procedure management system 1 according to an embodiment.

FIG. 1 is a schematic diagram of a viewing procedure management system 1 according to an embodiment. The viewing procedure management system 1 according to the present embodiment includes multiple patient examination nodes 2 and multiple authentication nodes 3 connected through a communication line 5 such as the Internet. Each patient examination node 2 generates examination data based on an examination of a patient. The examination data herein refers to a medical record created based on the examination of the patient by a doctor and converted to data. The medical record includes test images, test values, and the doctor's notes. As described later, each patient examination node 2 can store multiple data blocks in a blockchain format. Each patient examination node 2 receives and stores a new data block generated by an authentication node 3 in a manner described later and then transmitted through the communication line 5.

Each patient examination node 2 is connected to a data server 4 dedicated to the connected patient examination node 2. Each patient examination node 2 generates patient examination data, stores the patient examination data into the corresponding data server 4, and reads the patient examination data from the data server 4 and views the data as appropriate. To view patient examination data generated by another patient examination node 2, a patient examination node 2 transmits a message requesting viewing of the patient examination data to the other patient examination node 2. The patient examination node 2 requesting viewing of the patient examination data generated by another patient examination node 2 is hereafter referred to as a request node 2*a*, the patient examination data being requested by the request node 2*a* as target examination data, and the patient examination node 2 being the generator of the target examination data as a generation node 2*b*.

In the present embodiment, the patient examination nodes 2 are connected to the respective data servers 4. In some embodiments, for example, multiple patient examination nodes 2 may be connected to a data server 4 that is shared by these patient examination nodes 2, and may each generate patient examination data to be stored into the data server 4. All patient examination nodes 2 may be connected to a data server 4 that is a central data server, and may each generate patient examination data to be stored into the data server 4. The data server 4 in the present embodiment corresponds to a database in one or more aspects of the present invention.

The multiple authentication nodes 3 are connected to the communication line 5. The authentication nodes 3 can communicate with the patient examination nodes 2 through the communication line 5 and each generate a data block each time a patient examination node 2 generates patient examination data or a generation node 2*b* permits viewing of patient examination data in response to a request from a request node 2*a*. Thus, each authentication nodes 3 compare the generated data block 10 with data blocks 10 generated by the other authentication nodes 3. When all these data blocks 10 match, the authentication nodes 3 transmit the data blocks to all the patient examination nodes 2. All the patient examination nodes 2 thus store multiple data blocks into the blockchain format. The authentication nodes 3 also store the data blocks in the blockchain format.

In the present embodiment, the authentication nodes 3 do not examine patients and do not generate examination data and thus are not connected to the data servers 4 in the example shown in FIG. 1. In some embodiments, the authentication nodes 3 may examine patients and generate patient examination data. In this case, the authentication nodes 3 are connected to the data servers 4, which can store the patient examination data generated by the authentication nodes 3.

In this case, a patient to be examined at the patient examination node 2 may install a dedicated application on a patient terminal 6 such as a smartphone to connect to the viewing procedure management system 1 through the communication line 5. The patient may also use a web browser on the patient terminal 6 to connect to the viewing procedure management system 1.

Figure 2:
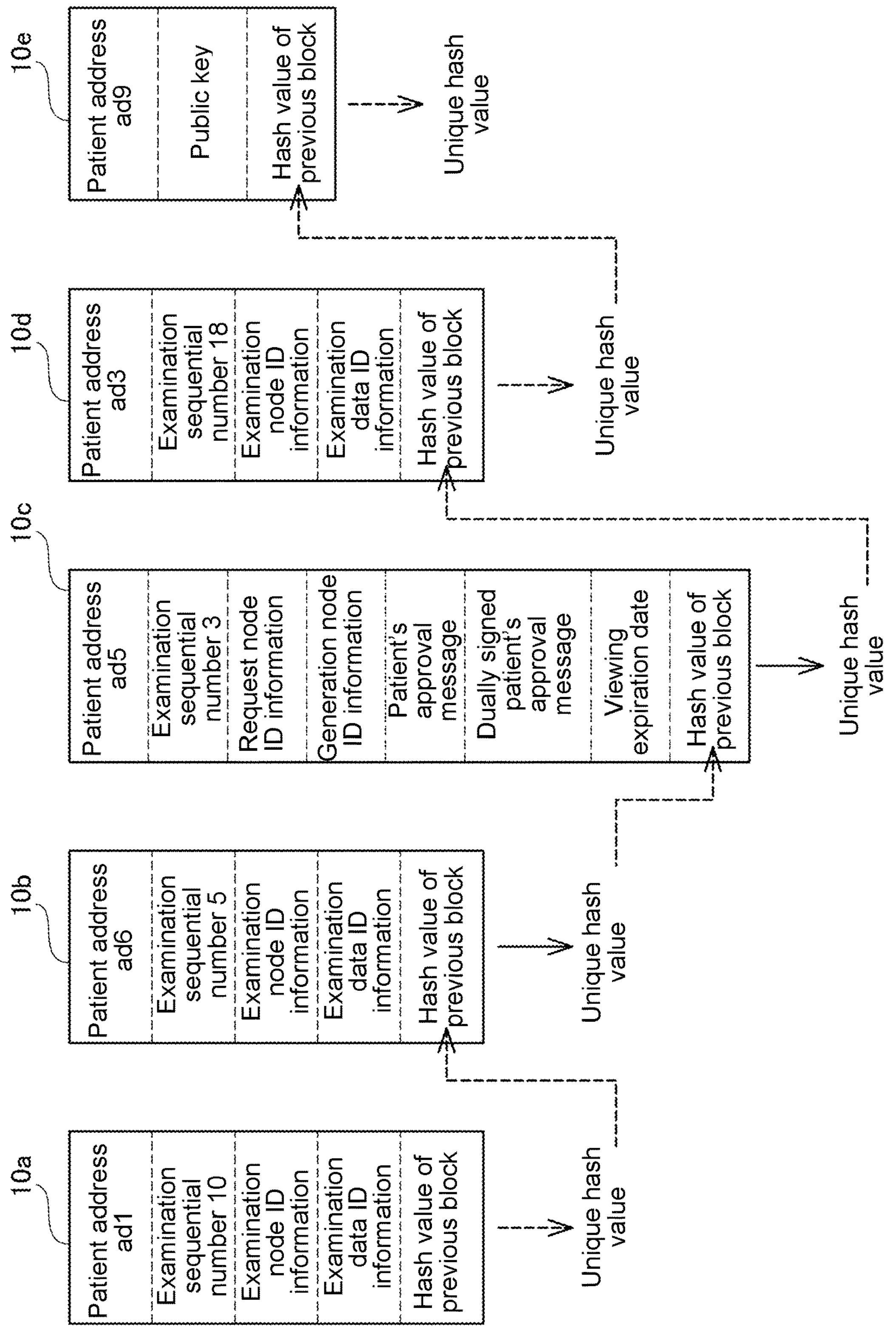
FIG. 2 is an example diagram describing multiple data blocks 10 stored in a patient examination node 2 or an authentication node 3 in a blockchain format.

FIG. 2 is an example diagram describing multiple data blocks 10 stored in a patient examination node 2 or an authentication node 3 in the blockchain format. The example in FIG. 2 conceptually shows five sets of data blocks 10*a* to 10*e* stored in the blockchain format. As shown in the figure, the data blocks 10 may not include data in the same format (in other words, the same type of data) and may include, for example, three types of data block 10 as in the example shown in FIG. 2. The three data blocks 10*a*, 10*b*, and 10*d* are of the same type in the same format, but the data block 10*c* and the data block 10*e* are of types different from the other data blocks.

The data blocks 10*a* to 10*d* are stored in the blockchain format, which is described below. For example, the data block 10*b* in FIG. 2 includes the hash value of the previous data block 10*a*. As known, the hash value is a value obtained by performing a specific operation called a hash function on data. The hash function converts data with any size and returns a hash value with a fixed data length. The harsh function convers data at least partially different from other data and returns a harsh value completely different from the hash value resulting from the other data. The original data cannot be reconstructed from any hash value. Each harsh value uniquely corresponds to the original data and uniquely represents the original data before conversion.

In FIG. 2, the hash value of the previous data block 10*a* is included in the data block 10*b*, and the hash value of the data block 10*b* is included in the subsequent data block 10*c*. The hash value of the data block 10*c* is included in the subsequent data block 10*d*, and the hash value of the data block 10*d* is included in the subsequent data block 10*e*. In this manner, the five data blocks 10*a* to 10*e* form a chain, with each data block connecting to another block. This state is referred to as the blockchain format. Each patient examination node 2 or each authentication node 3 stores multiple data blocks 10 in this blockchain format. Although the data blocks connect to one another using the hash values as described in the present embodiment, this specifically means that each data block refers to the hash value of the previous data block that uniquely represents the previous data block. In some embodiments, the data blocks may connect to one another using information other than the hash values that can uniquely identify the previous data blocks, such as Uniform Resource Locations (URLs) or Uniform Resource Names (URNs) of the previous data blocks. The data blocks 10 are stored into the patient examination nodes 2 and the authentication nodes 3 in the manner described below.

Figure 3:
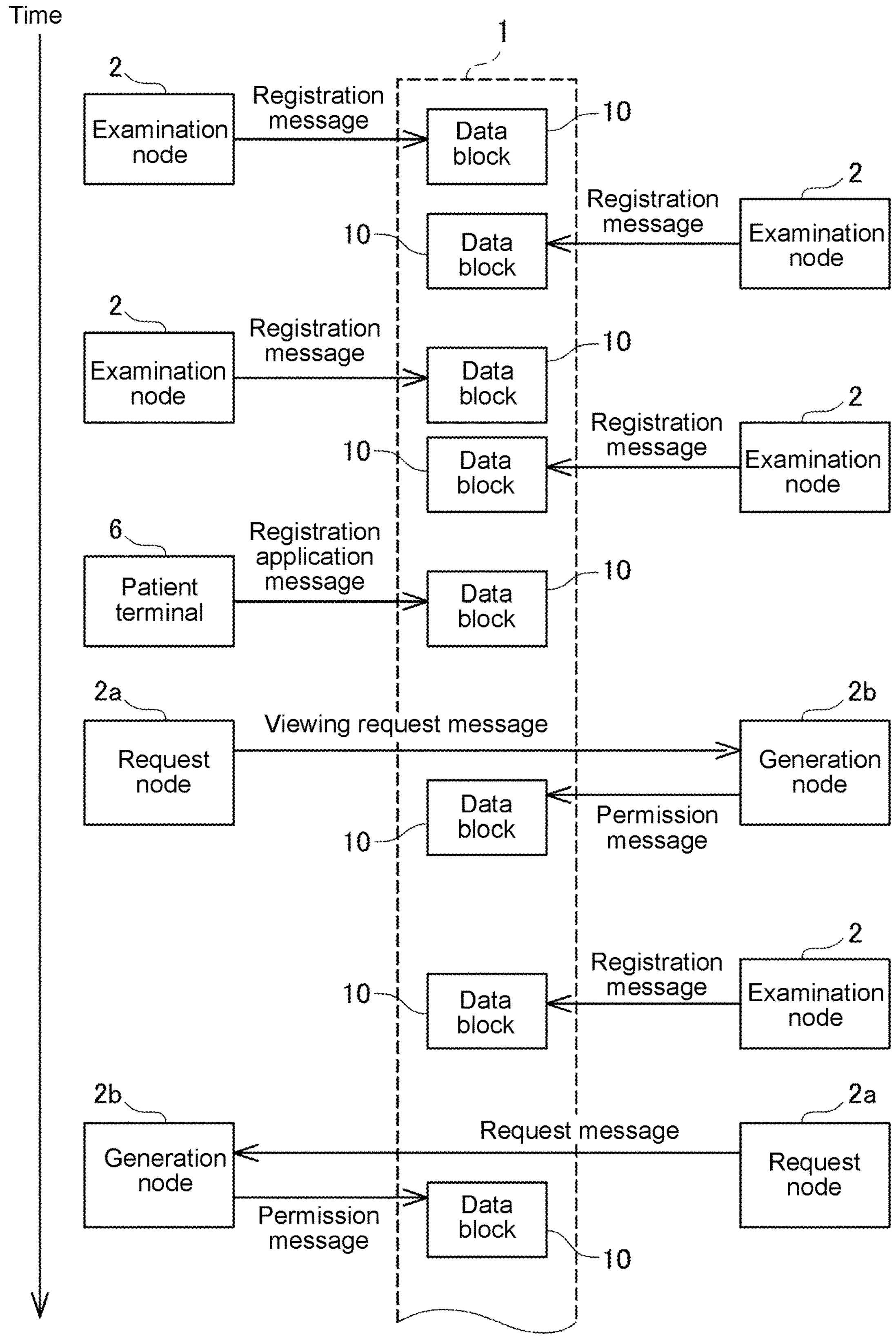
FIG. 3 is a conceptual diagram describing the data blocks 10 being stored into multiple patient examination nodes 2 and multiple authentication nodes 3 in the viewing procedure management system 1.

FIG. 3 is a conceptual diagram describing the data blocks 10 being stored into the patient examination nodes 2 and the authentication nodes 3. For example, a patient examination node 2 in the present embodiment generates patient examination data based on an examination of a patient, stores the patient examination data into the data server 4, and transmits a message (hereafter, a registration message) requesting registration of the patient examination data to the viewing procedure management system 1. The authentication nodes 3 in the viewing procedure management system 1 then authenticate the registration message. When the registration message is successfully authenticated, a data block 10 for registering the patient examination data is generated through the procedure performed by the authentication nodes 3. The data block 10 is transmitted from the authentication nodes 3 to the patient examination nodes 2 and stored into the authentication nodes 3 and the patient examination nodes 2. The data blocks 10*a*, 10*b*, and 10*d* in FIG. 2 are stored in this manner. The generation of the data block 10 will be described in detail later.

With the data block 10 stored, another patient examination node 2 may transmit a registration message for patient examination data to the viewing procedure management system 1. In this case, a new data block 10 is stored to follow the previously stored data block 10 in the blockchain format. In the example shown in FIG. 3, four data blocks 10 from four patient examination nodes 2 are stored in the blockchain format.

When the patient transmits a message (hereafter, a registration application message) applying for registration from the patient terminal 6 to the viewing procedure management system 1, the authentication nodes 3 in the viewing procedure management system 1 authenticate the registration application message. When the registration application message is successfully authenticated, a data block 10 for registering the patient is stored into the patient examination nodes 2 and the authentication nodes 3. The data block 10*e* in FIG. 2 is stored in this manner. The generation of such a data block 10 will be described in detail later.

When the request node 2*a* transmits, to the generation node 2*b*, a message (hereafter, a request message) requesting viewing of patient examination data, the generation node 2*b* transmits a message (hereafter, a permission message) requesting setting of a viewing right to the viewing procedure management system 1. The authentication nodes 3 in the viewing procedure management system 1 then authenticate the permission message. When the permission message is successfully authenticated, a data block 10 for setting the viewing right to the request node 2*a* is generated through the procedure performed by the multiple authentication nodes 3 and stored into the patient examination nodes 2 and the authentication nodes 3. The data block 10*c* in FIG. 2 is stored in this manner. The data block 10 with the viewing right set to the request node 2*a*, such as the data block 10*c*, may be hereafter referred to as the data block 10 with viewing permission. In the data block 10*c* in FIG. 2, a dually signed patient's approval message refers to a signature of a patient using a reference value and a signature of a generation node 2 added to the signature of the patient. A dually signed patient's approval message by the patient and the patient examination node 2 may be hereafter referred to as a dual signature of the patient and the examination node 2. The generation of the data block 10 with viewing permission will be described in detail later.

As described above, in the viewing procedure management system 1 according to the present embodiment, the patient examination node 2, the request node 2*a*, or the generation node 2*b* transmits a massage to (or through) the viewing procedure management system 1. The message is authenticated by the authentication nodes 3 and stored into the patient examination nodes 2 and the authentication nodes 3 in the blockchain format. In particular, the generation node 2*b* transmits, in response to a request from the request node 2*a*, the permission message including a dual signature of the patient (target patient) of the patient examination data and the generation node 2*b* to the authentication nodes 3. The authentication nodes 3 receive and authenticate the permission message, and generate the data block 10 with viewing permission (refer to the data block 10*c* in FIG. 2) when the permission message is successfully authenticated. Thus, when the dual signature of the target patient and the generation node 2*b* is not successfully authenticated, the data block 10 with viewing permission is not generated or stored into the patient examination nodes 2 or the authentication nodes 3. The permission message may include separate signatures of the target patient and the generation node 2*b*, in place of the dual signature of the target patient and the generation node 2*b*, to be authenticated by the authentication nodes 3 receiving the permission message.

This prevents the request node 2*a* from viewing the target examination data without confirming the data block 10 with viewing permission and allows the request node 2*a* to easily prove, later, that the target examination data has been viewed with the consent of the target patient and the generation node 2*b*. Additionally, the data block 10 stored in the blockchain format is difficult to alter later. Further, with the multiple patient examination nodes 2 and the multiple authentication nodes 3 storing the same data block 10, alteration of the data block 10 stored in a patient examination node 2 is easily detected by comparing the data block 10 with the data blocks 10 stored in the other patient examination nodes 2. This allows the data block 10 with viewing permission to be easily proved as not being altered. Thus, the request node 2*a* can avoid, by requesting viewing of patient examination data through the viewing procedure management system 1, being involved in an unexpected legal action.

The generation node 2*b* can also avoid, by permitting the request node 2*a* to view the patient examination data through the viewing procedure management system 1, being involved in an unexpected legal action. The data block 10 with viewing permission includes the signature of the target patient. Thus, when the generation node 2*b* transmits, to permit viewing by the request node 2*a*, a message without the signature of the target patient to the viewing procedure management system 1, the message is not successfully authenticated by the authentication nodes 3, and the data block 10 with viewing permission is thus not generated. The generation node 2*b* permitting the request node 2*a* to view the target examination data through the viewing procedure management system 1 can thus avoid permitting viewing of the target examination data without the consent of the patient and thus avoid being involved in an unexpected legal action.

To obtain such advantageous effects, the request node 2*a* simply requests viewing of the patient examination data through the viewing procedure management system 1, and the generation node 2*b* simply permits viewing in response to the request through the viewing procedure management system 1. This allows sufficient use of the patient examination data without increasing the burden on the request node 2*a* and the generation node 2*b*. The viewing procedure management system 1 for achieving these will be described in detail below.

As described above, the authentication nodes 3 in the present embodiment authenticate the permission message and generate the data block 10 with viewing permission when the permission message is successfully authenticated. In some embodiments, for simplicity, the authentication nodes 3 may generate the data block 10 with viewing permission without authenticating the received permission message. In this case, the data block 10 with viewing permission without permission from, for example, the generation node 2*b* is stored in the blockchain format but does not cause practical issues as described below.

In an example, the request node 2*a* might generate and transmit an unauthorized permission message to the authentication nodes 3 without permission from, for example, the generation node 2*b*. If the authentication nodes 3 did not authenticate the permission message, an unauthorized data block 10 with viewing permission, which is not permitted, were generated and were stored in the blockchain format. In this case, however, the generation node 2*b* can detect any viewing request from the request node 2*b* that has not been permitted, and thus can avoid providing requested patient examination data, thus causing no practical issue. If such examination were not performed as well, unauthorized viewing of the patient examination data by the request node 2*a* based on the data block 10 with viewing permission could be detected by examining the data block 10 with viewing permission later. The request node 2*a* is thus unlikely to generate an unauthorized permission message to cause the authentication nodes 3 to generate an unauthorized data block 10 with viewing permission. The authentication nodes 3 may thus generate the data block 10 with viewing permission without authenticating the received permission message for simplicity.

B. Internal Structures of Patient Examination Node 2 and Authentication Node 3

Figure 4:
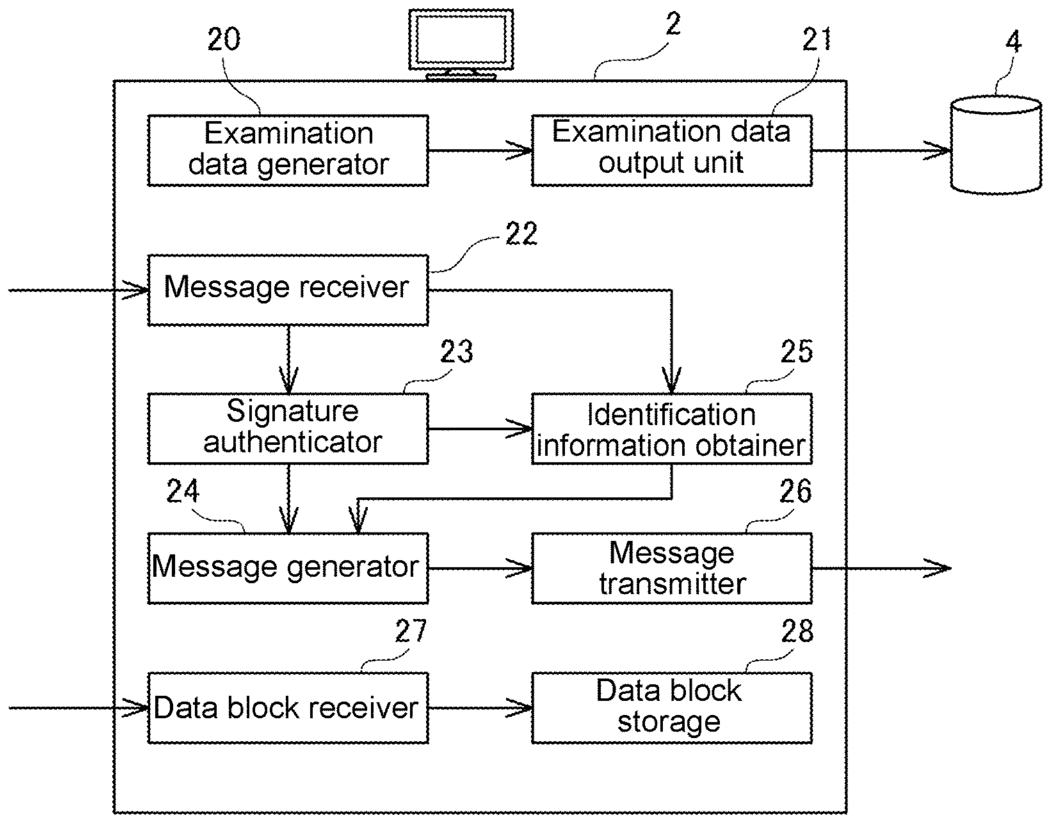
FIG. 4 is a block diagram of the patient examination node 2 showing its internal structure.

FIG. 4 is a block diagram of a patient examination node 2 in the viewing procedure management system 1 according to the present embodiment, showing its internal structure. As shown in the figure, the patient examination node 2 includes, for example, an examination data generator 20, an examination data output unit 21, a message receiver 22, a signature authenticator 23, a message generator 24, an identification information obtainer 25, a message transmitter 26, a data block receiver 27, and a data block storage 28. These units are conceptual representations of functions included in the patient examination node 2. The patient examination node 2 may thus not include devices corresponding to these units. These units may be implemented as a software program executable by a microcomputer incorporated in the patient examination node 2 or as hardware using, for example, a large-scale integration (LSI) circuit or an integrated circuit (IC) included in the patient examination node 2. These units may also be implemented by combining the software program and the hardware.

The examination data generator 20 generates patient examination data by reading and converting a medical record based on an examination of a patient to data, and outputs the generated patient examination data to the examination data output unit 21. The examination data output unit 21 is connected to the data server 4 and stores the patient examination data received from the examination data generator 20 into the data server 4.

The message receiver 22 is connected to the communication line 5 such as the Internet, receives a message transmitted through the communication line 5, and outputs the message to the signature authenticator 23 and the identification information obtainer 25. As described in detail later, the message received by the message receiver 22 may be, for example, the request message requesting viewing of the patient examination data transmitted from the request node 2*a*.

When the received message includes a signature, the signature authenticator 23 authenticates the signature. When the message includes a signature of the patient, the signature authenticator 23 authenticates the signature of the patient. The signature authenticator 23 in the present embodiment thus corresponds to a patient signature authenticator in one or more aspects of the present invention. When the signature of the patient is successfully authenticated, the signature authenticator 23 outputs the result of the authentication to the message generator 24 and the identification information obtainer 25.

When receiving the result of successful authentication, the message generator 24 generates a message corresponding to the received message. For example, when receiving the request message from the request node 2*a*, the message generator 24 generates the permission message requesting generation of the data block 10 with viewing permission. In another case for requesting viewing of the patient examination data through the generation node 2*b*, the message generator 24 generates the request message. For generating these messages, predetermined information (hereafter, identification information) is to be used, and the identification information is provided from the identification information obtainer 25. More specifically, after receiving the notification of successful authentication by the signature authenticator 23, the identification information obtainer 25 extracts the identification information from the message received from the message receiver 22 and outputs the identification information to the message generator 24. In the patient examination node 2 as the generation node 2*b*, the message generator 24 generates the permission message. The message generator 24 in the present embodiment thus corresponds to a permission message generator in one or more aspects of the present invention.

The message generator 24 outputs the message generated in this manner to the message transmitter 26. The message transmitter 26 is connected to the communication line 5 and transmits the message to the patient examination nodes 2 and the authentication nodes 3 connected to the communication line 5. In the patient examination node 2 as the request node 2*a*, the message transmitter 26 transmits the request message. In the patient examination node 2 as the generation node 2*b*, the message transmitter 26 transmits the permission message. The message generator 24 in the present embodiment thus corresponds to a request message transmitter and a permission message transmitter in one or more aspects of the present invention.

The data block receiver 27 is also connected to the communication line 5, receives a new data block 10 transmitted from the authentication nodes 3, and outputs the data block 10 to the data block storage 28. After receiving the data block 10 from the data block receiver 27, the data block storage 28 stores the data block 10 in the blockchain format described above with reference to FIG. 2.

Figure 5:
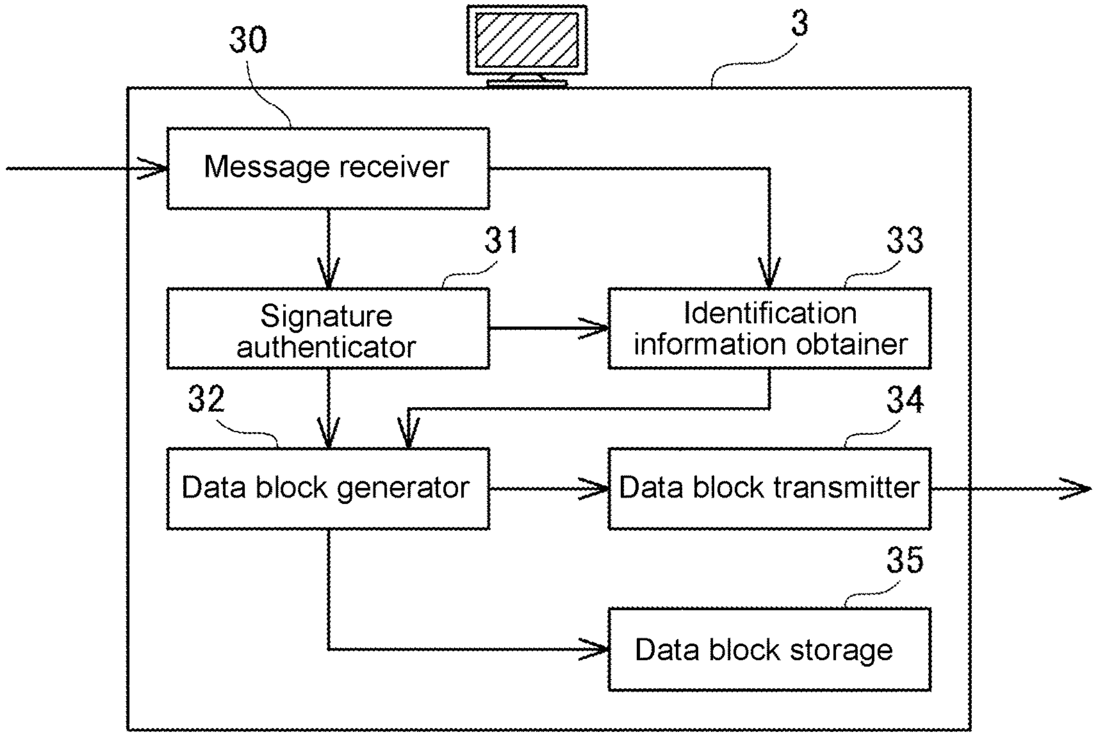
FIG. 5 is a block diagram of the authentication node 3 showing its internal structure.

FIG. 5 is a block diagram of an authentication node 3 in the viewing procedure management system 1 according to the present embodiment, showing its internal structure. As shown in the figure, the authentication node 3 includes, for example, a message receiver 30*a*, a signature authenticator 31, a data block generator 32, an identification information obtainer 33, a data block transmitter 34, and a data block storage 35. These units are conceptual representations of functions included in the authentication node 3. The authentication node 3 may thus not include devices corresponding to these units. These units may be implemented as a software program executable by a microcomputer incorporated in the authentication node 3 or as hardware using, for example, an LSI circuit or an IC included in the authentication node 3. These units may also be implemented by combining the software program and the hardware.

The message receiver 30 in the authentication node 3 is connected to the communication line 5 such as the Internet and, after receiving a message transmitted through the communication line 5, outputs the message to the signature authenticator 31 and the identification information obtainer 33. As described in detail later, the message received by the message receiver 30 in the authentication node 3 may be, for example, the registration application message from the patient terminal 6, or the registration message or the permission message from the patient examination node 2.

When the message received from the message receiver 30 includes a signature, the signature authenticator 31 in the authentication node 3 authenticates the signature. As described in detail later, the received message being the permission message from the generation node 2*b* includes the signature of the generation node 2*b*. In this case, the signature authenticator 31 in the authentication node 3 authenticates the signature of the generation node 2*b*. The signature authenticator 31 in the present embodiment thus corresponds to a generation node signature authenticator in one or more aspects of the present invention. When the signature of the generation node 2*b* is successfully authenticated, the signature authenticator 31 outputs the result of the authentication to the data block generator 32 and the identification information obtainer 33. When the message received from the message receiver 30 being the registration application message from the patient terminal 6, the signature authenticator 31 in the authentication node 3 authenticates the signature of the patient included in the registration application message.

When receiving the result of successful authentication, the data block generator 32 generates a block data 10 corresponding to the message. For generating the data block 10, predetermined identification information is to be used, and the identification information is provided from the identification information obtainer 33. More specifically, after receiving the notification of successful authentication by the signature authenticator 31, the identification information obtainer 33 extracts the identification information from the message received from the message receiver 30 and outputs the identification information to the data block generator 32. The data block generator 32 generates the data block 10 based on the identification information received in this manner. The viewing procedure management system 1 includes multiple authentication nodes 3 (refer to FIG. 1), and the data block generator 32 in each authentication node 3 generates the data block 10. The data block generators 32 in the authentication nodes 3 then compare the generated data blocks 10 with one another, and perform determination for any inconsistency among the data blocks 10 through the procedure performed using the majority, and determine a data block 10 to be used.

The data block generator 32 outputs the data block 10 confirmed in this manner to the data block transmitter 34 and the data block storage 35. The data block transmitter 34 is connected to the communication line 5 and transmits the data block 10 to the patient examination nodes 2 connected to the communication line 5. The data block 10 transmitted in this manner is received by the data block receiver 27 in each patient examination node 2 described above with reference to FIG. 4 and stored into the data block storage 28 in the blockchain format.

The viewing procedure management system 1 according to the present embodiment includes the multiple patient examination nodes 2 and the multiple authentication nodes 3 each having the internal structure described above and connected through the communication lines 5. This allows the patient examination nodes 2 and the authentication nodes 3 to operate as described below.

C. Registering at Patient Terminal 6

In the viewing procedure management system 1 according to the present embodiment, the patient to be examined at the patient examination node 2 registers with the viewing procedure management system 1 in advance. To register the patient with the viewing procedure management system 1, the patient terminal 6 held by the patient and the authentication nodes 3 perform the processing described below.

Figure 6:
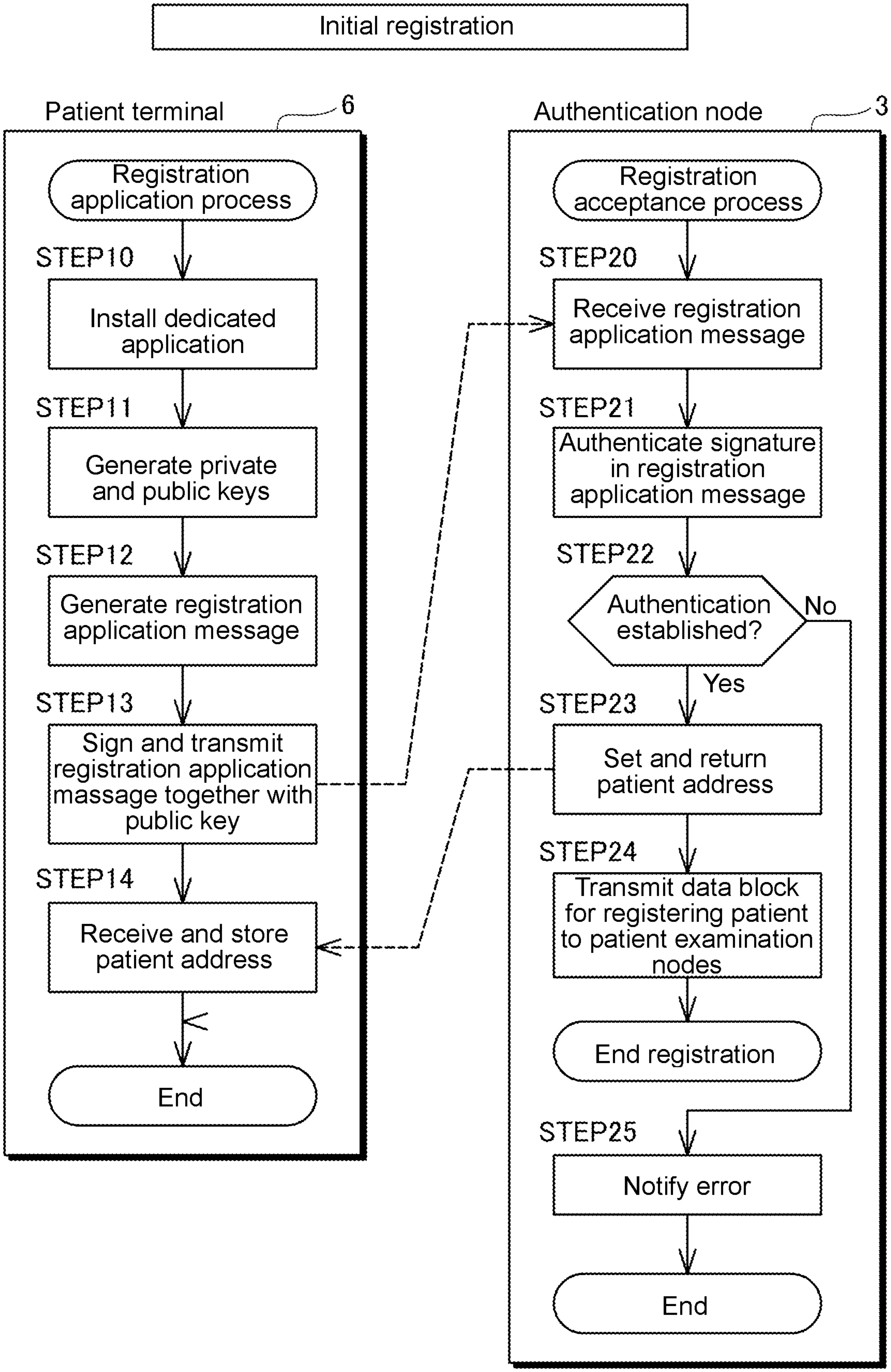
FIG. 6 is a flowchart of processing performed by a patient terminal 6 and the authentication node 3 when a patient registers with the viewing procedure management system 1.

FIG. 6 is a flowchart of processing performed by the patient terminal 6 and the authentication node 3 when the patient to be examined at the patient examination node 2 registers with the viewing procedure management system 1. As shown in the figure, to register the patient with the viewing procedure management system 1, a registration application process is performed by the patient terminal 6, and a registration acceptance process is performed by the authentication nodes 3. In the registration application process performed by the patient terminal 6, a dedicated application is first installed on the patient terminal 6 (STEP 10). The installed dedicated application is activated to generate a private key and a public key (STEP 11). When a patient generates their own private key, the dedicated application automatically generates the public key that pairs with the private key. In the present embodiment, the private key and the public key are generated using the dedicated application installed on the patient terminal 6. In some embodiments, the private key and the public key may be generated differently using, for example, an extension application that operates in a viewing application (e.g., a web browser) for the patient terminal 6.

The patient then generates a message (a registration application message) expressing an intention of registration with the viewing procedure management system 1 using the dedicated application (STEP 12). The dedicated application electronically signs the registration application message using the private key and transmits the message, together with the public key, to the viewing procedure management system 1 (STEP 13). The message is received by the authentication nodes 3 in the viewing procedure management system 1.

The registration acceptance process described below is performed by each authentication node 3. The authentication node 3 first receives the registration application message transmitted from the patient terminal 6 (STEP 20). The authentication node 3 then authenticates the signature in the registration application message (STEP 21). In this step, the registration application message signed electronically with the patient's private key is transmitted from the patient terminal 6 together with the public key. When the signed message is correctly decrypted with the public key to the registration application message, the message is determined to have been signed by a person (in this case, the patient) who has the private key pairing with the public key transmitted together with the message. Further, the message indicates the intention of registration with the viewing procedure management system 1.

Thus, when the message is successfully authenticated (Yes in STEP 22), the authentication node 3 sets an address of the patient in the viewing procedure management system 1 (hereafter, a patient address) and returns the address to the patient terminal 6 (STEP 23). The patient terminal 6 receives and stores the patient address returned in this manner into the patient terminal 6 (STEP 14), and ends the registration application process.

After returning the patient address to the patient terminal 6 (STEP 23), the authentication node 3 generates a data block 10 for registering the patient address, and compares the generated data block 10 with data blocks 10 generated by the other authentication nodes 3. When all these data blocks 10 match, the authentication node 3 determines to use the generated data block 10. When the generated data block 10 does not match any of the data blocks 10 generated by the other authentication nodes 3, the authentication node 3 determines to use one of the data blocks 10 having the highest match with the other data blocks 10. The authentication node 3 then transmits the determined data block 10 to all the patient examination nodes 2 (STEP 24) and ends the registration acceptance process. In STEP 24, the data block 10 is also stored into the authentication nodes 3. Thus, the data block 10 for registering the patient address is stored into the patient examination nodes 2 (and the authentication nodes 3) in the blockchain format. The data block 10(*e*) in FIG. 2 is stored in this manner. In contrast, when the message is not successfully authenticated (No in STEP 22), the authentication node 3 transmits an error message to the patient terminal 6 (STEP 25) and ends the registration acceptance process.

In the above example, the patient terminal 6 generates and electronically signs the registration application message and transmits the message to the authentication node 3. In some embodiments, the patient terminal 6 may transmit the registration application message without a signature and may receive a message for establishing authentication from the authentication node 3, and may transmit a challenge code for a signature to the patient terminal 6. The patient terminal may then electronically sign the challenge code and return the signed challenge code to the authentication node 3.

In the above example, the dedicated application on the patient terminal 6 is activated without authentication. In some embodiments, the dedicated application may be activated with authentication using a password or biometric authentication. This can prevent a third party from applying for registration without permission or changing the registered public key.

D. Registering Patient Examination Data

Figure 7:
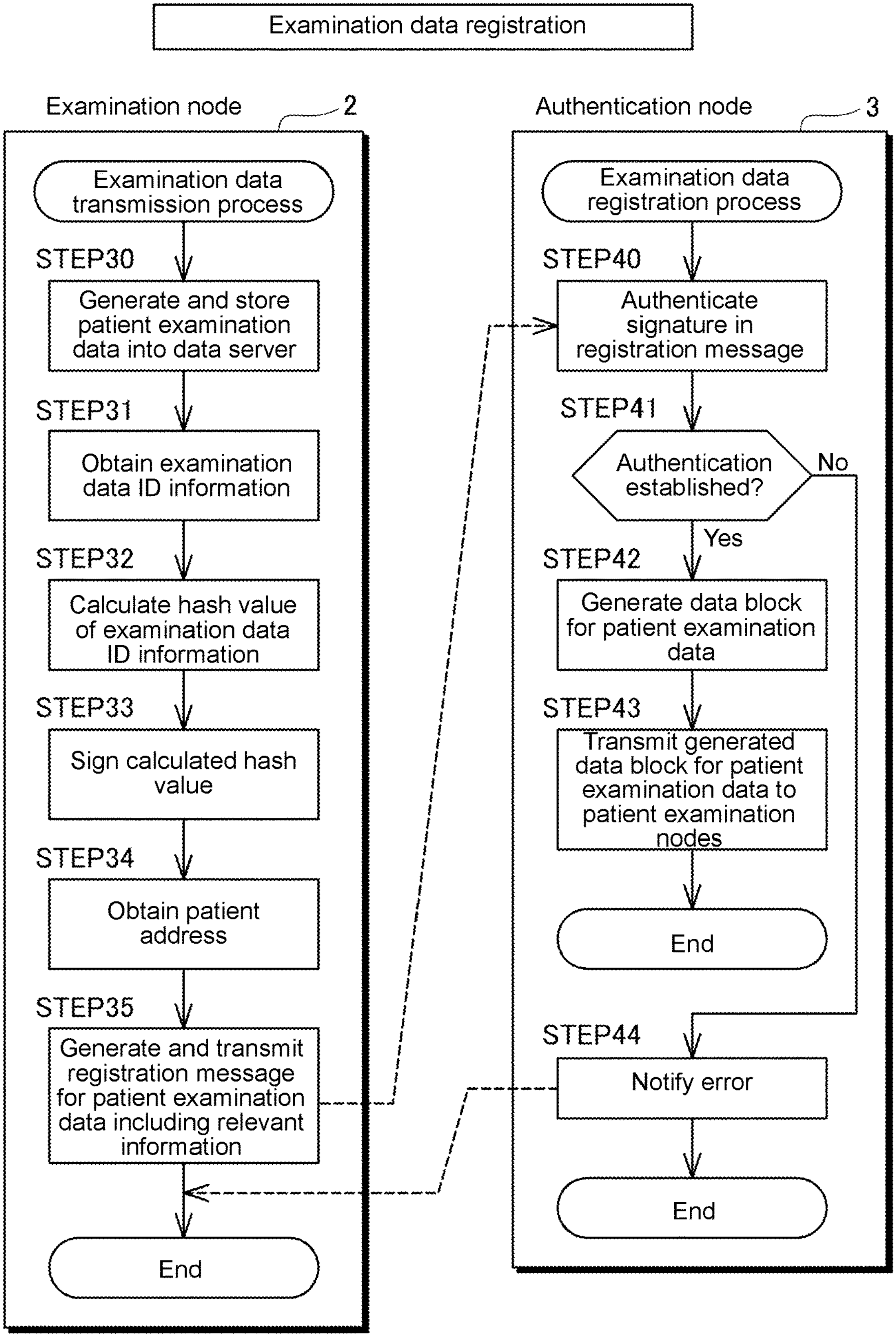
FIG. 7 is a flowchart of processing performed by the patient examination node 2 and the authentication node 3 when the patient examination node 2 registers patient examination data with the viewing procedure management system 1.

FIG. 7 is a flowchart of processing performed by the patient examination node 2 and the authentication node 3 when the patient examination node 2 registers patient examination data with the viewing procedure management system 1. As shown in the figure, to register the patient examination data with the viewing procedure management system 1, an examination data transmission process is performed by the patient examination node 2, and an examination data registration process is performed by the authentication node 3. In the examination data transmission process, the patient examination node 2 first converts a medical record to the patient examination data and stores the patient examination data into the data server 4 (STEP 30). The patient examination node 2 then obtains information to be used for identifying the stored patient examination data (hereafter, examination data ID information) (STEP 31). The examination data ID information identifies the patient examination data to read the patient examination data from the data server 4 later. The examination data ID information may be a URL indicating the storage location of the patient examination data or a URN as a specific name for the patient examination data.

After obtaining the examination data ID information, the patient examination node 2 calculates the hash value of the examination data ID information (STEP 32). As described above, the hash value is obtained by applying the hash function to data. Each hash value uniquely corresponds to the original data. After obtaining the hash value, the patient examination node 2 electronically signs the hash value using a private key of the patient examination node 2 (STEP 33). The patient examination node 2 generates the private key and a public key when registering with the viewing procedure management system 1 and registers the public key with the viewing procedure management system 1.

The patient examination node 2 then obtains the patient address of the target patient (STEP 34). The patient address is uniquely assigned to the patient when the patient registers with the viewing procedure management system 1, and is stored into the dedicated application on the patient terminal 6 held by the patient (refer to STEP 14 in FIG. 6). The patient address may be manually input on the display of the patient examination node 2 while the address displayed on the patient terminal 6 is being referred to, or may be obtained through communication between the patient terminal 6 and the patient examination node 2.

Figure 8:
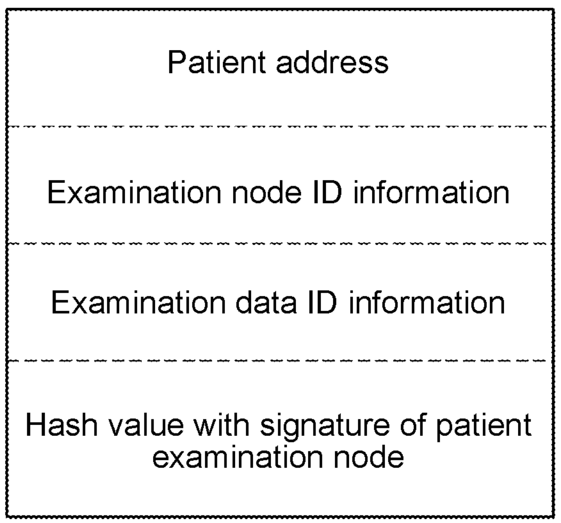
FIG. 8 is a diagram describing multiple pieces of information included in a registration message for registering the patient examination data.

With the above preparations, the patient examination node 2 generates a registration message (namely, a message requesting registration of the patient examination data) including the information described below and transmits the message to the viewing procedure management system 1 (STEP 35). FIG. 8 is a diagram of information included in the registration message. As shown in the figure, the registration message includes the patient address, patient examination node ID information, the examination data ID information, and the hash value with a signature of the patient examination node 2. The patient address is obtained in STEP 34, the examination data ID information is obtained in STEP 31, and the hash value with the signature is obtained in STEP 32 in FIG. 7. The patient examination node ID information identifies the patient examination node 2 (e.g., an address of the patient examination node 2 in the viewing procedure management system 1). The patient examination node 2 stores the patient examination node ID information when registering with the viewing procedure management system 1. In STEP 35 in FIG. 7, the patient examination node 2 generates the registration message including such information and transmits the message to the viewing procedure management system 1. After transmission, the patient examination node 2 waits for a predetermined period and confirms that an error message (described later) is not received and then ends the examination data transmission process.

The registration message transmitted from the patient examination node 2 to the viewing procedure management system 1 is received by the authentication node 3. After receiving the registration message, the authentication node 3 performs the examination data registration process described below. The authentication node 3 first authenticates the signature in the registration message (STEP 40). As described above, the registration message includes the patient examination node ID information, the examination data ID information, and the electronically signed hash value of the examination data ID information. The authentication node 3 decrypts the signed hash value using the public key of the patient examination node 2 obtained based on the patient examination node ID information. The authentication node 3 also calculates the hash value of the examination data ID information included in the registration message. The calculated hash value is then compared with the hash value obtained by decrypting. When the two values match, the authentication node 3 determines that the authentication is successful (Yes in STEP 41). When the two values do not match, the authentication node 3 determines that the authentication is not successful (No in STEP 41).

Figure 9:
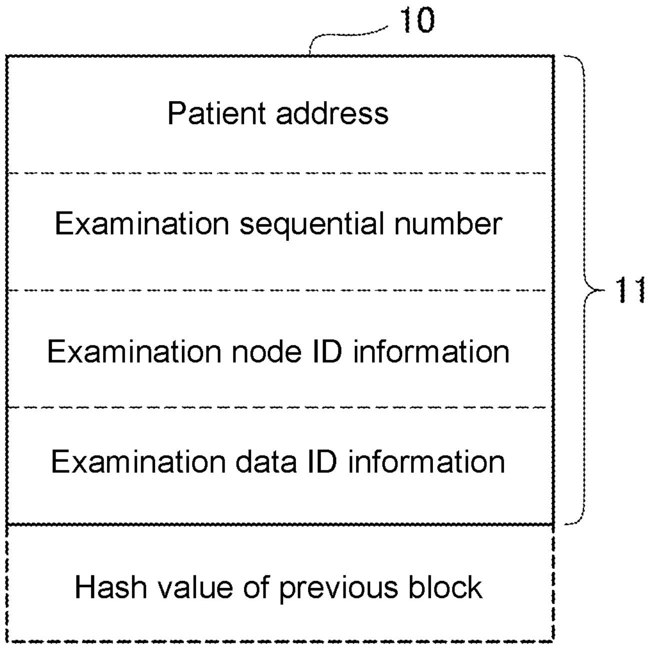
FIG. 9 is a diagram describing a data block 10 generated by the authentication node 3 for registering the patient examination data.

When the authentication is successful (Yes in STEP 41), the authentication node 3 generates the data block 10 for the patient examination data (STEP 42). FIG. 9 is a diagram describing the data block 10 generated by the authentication node 3. As compared with data (information included in the registration message) shown in FIG. 8, the data block 10 in FIG. 9 includes a data set (hereafter, a data set 11) including the same information as in the registration message except an examination sequential number being included and the signed hash value being deleted, and further includes the hash value of the previous data block 10.

The examination sequential number indicates the number of times the patient with the patient address has been examined (at any patient examination node 2). As shown in the data blocks 10*a* and 10*b* in FIG. 2, each time the patient is examined at the patient examination node 2, a data block 10 is stored into the patient examination node 2 and the authentication node 3 in the block chain format. The data block 10 includes the patient address of the target patient. Thus, the authentication node 3 can count the number of examinations for each patient address by searching the stored multiple data blocks 10 and determine the number of times the patient has been examined. The examination sequential number for the N-th examination is N. In STEP 42 in FIG. 7, the authentication node 3 adds, to the data set 11 generated in this manner, the hash value of the previous data block 10 to generate the data block 10 for registering the patient examination data.

After generating the data block 10 in this manner, the authentication node 3 determines whether to use the generated data block 10 or to use the data block 10 having the highest match with the other data blocks based on the data blocks generated by the other authentication nodes 3. The authentication node 3 then transmits the determined data block 10 to all the patient examination nodes 2 (STEP 43), and ends the registration acceptance process. Thus, the data block 10 for registering the patient examination data is stored into the patient examination nodes 2 in the blockchain format. In STEP 43, the data block 10 is also stored into the authentication nodes 3. After transmitting and storing the data block 10, the authentication node 3 ends the examination data registration process.

As described above, when the patient is examined at the patient examination node 2 and the patient examination node 2 generates the patient examination data, the above processing is performed to store the data block 10 such as the data blocks 10*a* and 10*b* in FIG. 2 into the patient examination nodes 2 and the authentication nodes 3. For the patient examination node 2 at which the patient is examined to view the examination data generated by another patient examination node 2, the processing described below is performed to generate the data block 10 with viewing permission such as the data block 10*c* shown in FIG. 2.

E. Requesting Viewing of Examination Data

Figure 10:
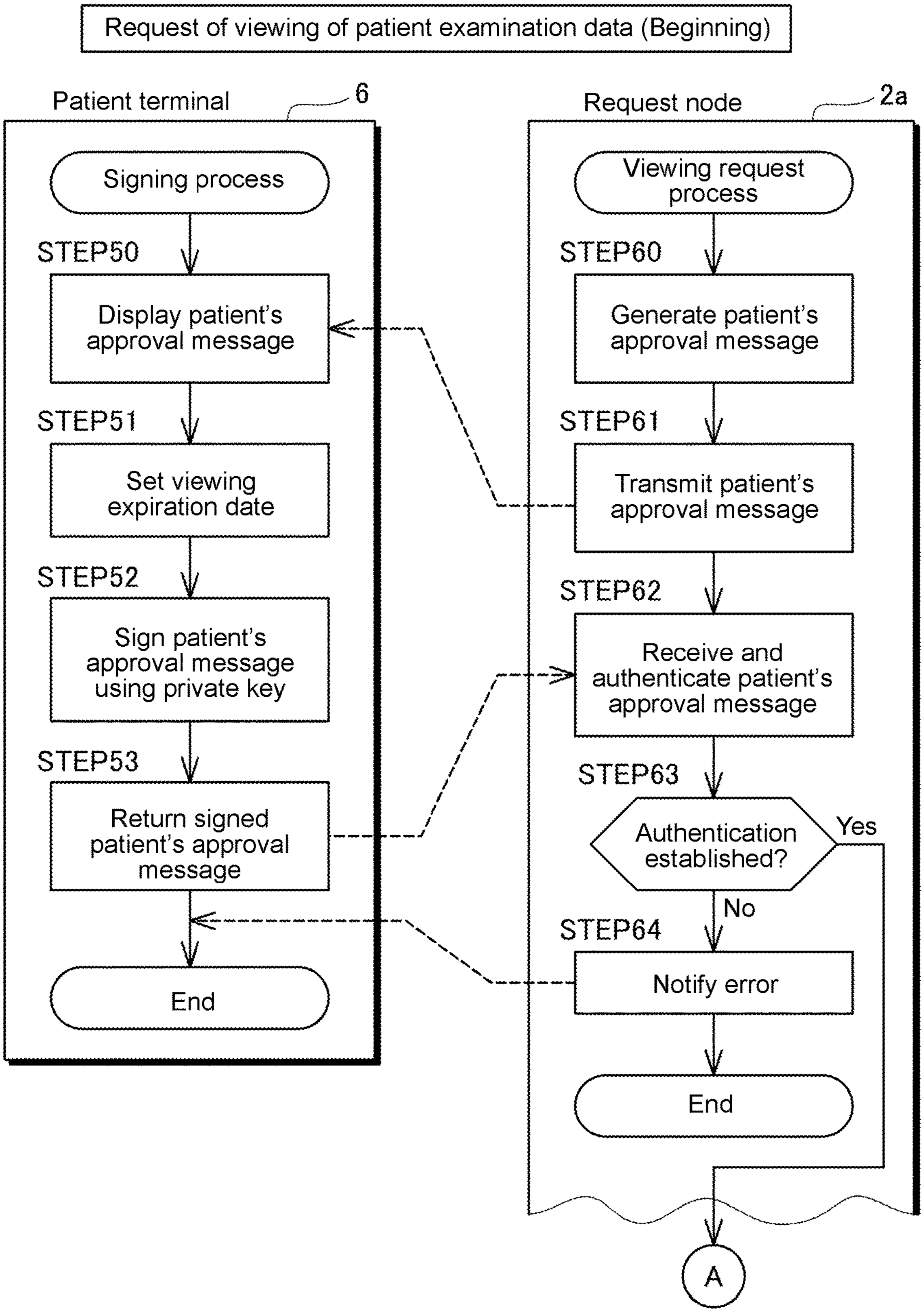
FIG. 10 is a flowchart of processing performed by the patient terminal 6 and a request node 2*a* when the request node 2*a* requests viewing of the patient examination data to a generation node 2*b*.
Figure 11:
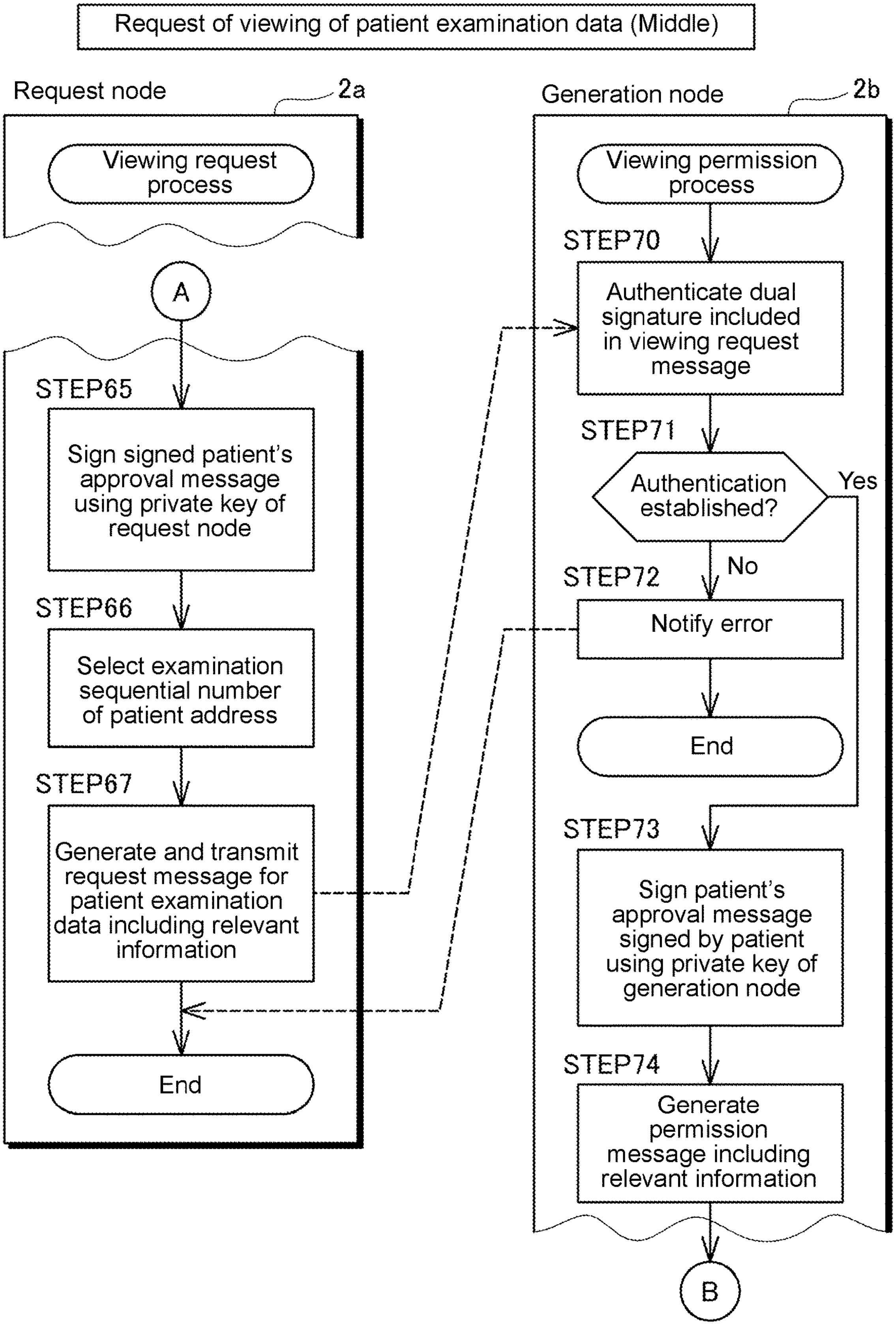
FIG. 11 is a flowchart of processing performed by the request node 2*a* and the generation node 2*b* when the request node 2*a* requests viewing of the patient examination data through the generation node 2*b*.
Figure 12:
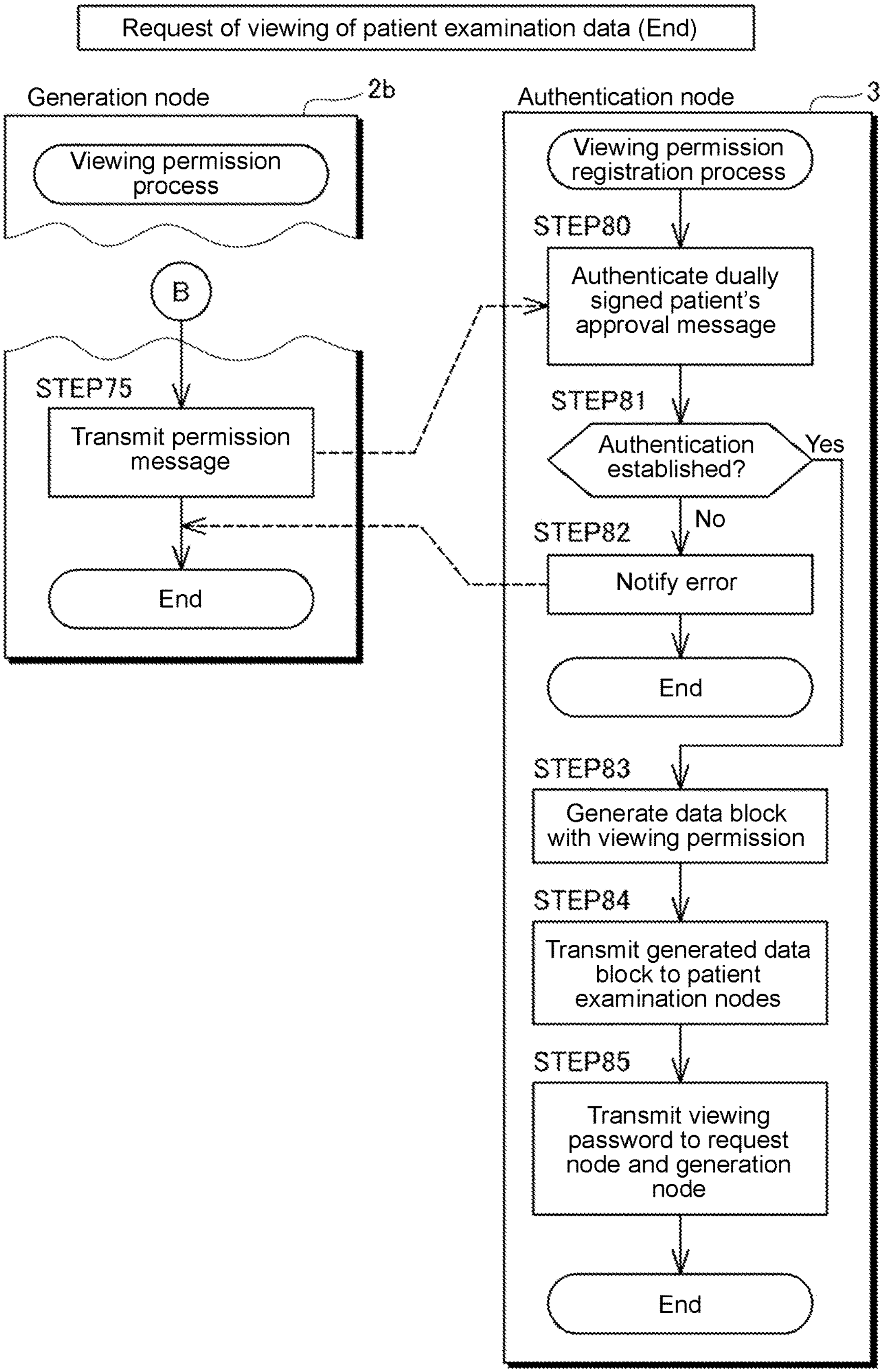
FIG. 12 is a flowchart of processing performed by the generation node 2*b* and the authentication node 3 when the request node 2*a* requests viewing of the examination data through the generation node 2*b*.

FIGS. 10 to 12 are flowcharts of processing to generate and store the data block 10 with viewing permission into the patient examination nodes 2 and the authentication nodes 3. FIG. 10 shows processing performed by the request node 2*a* (the patient examination node 2 requesting viewing of the patient examination data) and the patient terminal 6 held by the target patient (the patient of the patient examination data to be viewed). FIG. 11 shows processing performed by the request node 2*a* and the generation node 2*b* (the patient examination node 2 that has generated the patient examination data to be viewed). FIG. 12 shows processing performed by the generation node 2*b* and the authentication node 3.

As shown in FIG. 10, to generate the data block 10 with viewing permission, the request node 2*a* first starts a viewing request process, and the patient terminal 6 starts a signing process in response to the request node 2*a*. After starting the viewing request process, the request node 2*a* generates a patient's approval message (STEP 60). FIG. 13 is a diagram describing an example of the patient's approval message. As shown in the figure, the patient's approval message indicates an approval from the target patient for the request node 2*a* to view the target examination data (the patient examination data to be viewed). After generating the patient's approval message, the request node 2*a* transmits the patient's approval message to the patient terminal 6 held by the target patient (STEP 61).

The viewing may be in a manner in which the patient examination data can be viewed on a display but is not stored into the viewer's node, a manner in which the examination data viewed on the display is stored into the viewer's node for later viewing, and a manner in which the examination data is transmitted to the viewer's node. The viewing herein refers to viewing performed in the manners described above.

After receiving the patient's approval message, the patient terminal 6 held by the target patient starts the signing process. In the signing process, the patient terminal 6 displays the patient's approval message (STEP 50). The target patient reads the displayed patient's approval message, inputs the date of approval when finding no objection to the message, and sets the viewing expiration date (STEP 51). The target patient then electronically signs the patient's approval message using the private key stored in the patient terminal 6 (STEP 52) and returns the signed message to the request node 2*a* (STEP 53). After returning the message, the patient terminal 6 waits for a predetermined period and confirms that an error message (described later) is not received, and ends the signing process. The patient's approval message in the present embodiment corresponds to signature data in one or more aspects of the present invention.

In the viewing request process, after receiving the signed patient's approval message returned from the patient terminal 6, the request node 2*a* authenticates the message using the public key of the target patient (STEP 62). The public key of the target patient is stored as a data block 10 in all the patient examination nodes 2 when the patient registers with the viewing procedure management system 1. Thus, the request node 2*a* decrypts the signed patient's approval message using the public key and determines whether the message is decrypted correctly to authenticate the message (STEP 63). When the message is decrypted correctly, the request node 2*a* determines that the authentication is successful (Yes in STEP 63) and starts the process described below with the generation node 2*b*. In contrast, when the message is decrypted incorrectly, the request node 2*a* determines that the authentication is not successful (No in STEP 63), transmits an error message indicating that the authentication is not successful to the patient terminal 6 (STEP 64), and ends the viewing request process.

When the patient's approval message signed by the patient terminal 6 is successfully authenticated (Yes in STEP 63), the request node 2*a* electronically signs the signed patient's approval message using its private key (STEP 65 in FIG. 11). As a result of this, the patient's approval message is dually signed by the patient terminal 6 and the request node 2*a*.

The request node 2*a* then selects the examination sequential number of the patient address to identify the patient examination data requested for viewing (STEP 66). More specifically, the request node 2*a* may not need to view all patient examination data of the target patient stored in the data server 4 for the generation node 2*b*. Thus, the request node 2*a* selects the examination sequential number of the patient address to identify the patient examination data requested for viewing. Without selecting the examination sequential number, the request node 2*a* has seemingly requested viewing of all examination data.

With the above preparations, the request node 2*a* generates a request message (namely, a message requesting viewing of the patient examination data) including the information described below and transmits the request message to the generation node 2*b* (STEP 67). FIG. 14 is a diagram describing the information included in the request message. As shown in the figure, the request message includes the patient address, the examination sequential number, request node ID information, the patient's approval message (not signed), the patient's approval message dually signed by the target patient and the request node 2*a*, and the viewing expiration date. The request node ID information identifies the request node 2*a* (e.g., the address of the request node 2*a* in the viewing procedure management system 1). The patient address can be obtained from the patient terminal 6 in examining the patient. The patient's approval message is generated by the request node 2*a* in STEP 60 in FIG. 10. The dually signed patient's approval message is obtained in STEP 65, and the examination sequential number is obtained in STEP 66 in FIG. 11. The viewing expiration date is obtained with the signed patient's approval message from the patient terminal 6 in STEP 62 in FIG. 10. Thus, the request node 2*a* generates the request message including the above information, and transmits the request message to the generation node 2*b* in the viewing procedure management system 1 (STEP 67). After transmission, the request node 2*a* waits for a predetermined period to confirm that an error message (described later) is not received and then ends the viewing request process.

In this example, the request node 2*a* transmits the request message including the request node ID information to the generation node 2*b* for identifying the generation node 2*b*. However, in many cases, the generation node 2*b* can obtain the request node ID information by analyzing the header of the transmitted request message. Thus, the request message may include the request node ID information substantially, rather than explicitly.

After receiving the request message transmitted from the request node 2*a*, the generation node 2*b* starts a viewing permission process as described below. The generation node 2*b* first authenticates the patient's approval message dually signed by the target patient and the request node 2*a* (STEP 70). The generation node 2*b* decrypts the dually signed patient's approval message using the public key of the request node 2*a*, and further decrypts the resultant message using the public key of the target patient. Because the request message received from the request node 2*a* includes the request node ID information and the patient address, the generation node 2*b* can obtain the public key of the request node 2*a* and the public key of the target patient.

When the message decrypted using the two public keys matches the original patient's approval message, the generation node 2*b* determines that the authentication is successful (Yes in STEP 71). In the present embodiment, the authentication can be determined to be successful when the decrypted message matches the patient's approval message. In some embodiments, the authentication may be determined to be successful when the decrypted patient's approval message is meaningful and may be determined not to be successful when the decrypted patient's approval message is a meaningless character string. This allows the request message transmitted from the request node 2*a* to exclude the patient's approval message, thus reducing the data volume of the request message.

When the authentication is successful, the generation node 2*b* determines that the request node 2*a* has requested viewing of the patient examination data with the approval of the target patient. In contrast, when the decrypted message does not match the original patient's approval message, the generation node 2*b* determines that the authentication is not successful (No in STEP 71). When the authentication is not successful, the request node 2*a* may have requested viewing of the examination data without the approval of the target patient, or another party different from the request node 2*a* may be pretending to be the request node 2*a* requesting viewing of the patient examination data. Thus, when the authentication is not successful (No in STEP 71), the generation node 2*b* transmits an error message indicating that the authentication is not successful to the request node 2*a* (STEP 72), and ends the viewing permission process.

In contrast, when the authentication is successful (Yes in STEP 71), the generation node 2*b* electronically signs, using a private key of the generation node 2*b*, the patient's approval message signed by the target patient to generate a dual signature of the target patient and the generation node 2*b* (STEP 73). The generation node 2*b* obtains the patient's approval message signed by the target patient when authenticating the dual signature of the target patient and the request node 2*a* in STEP 70.

The generation node 2*b* then generates the permission message including necessary information (STEP 74). More specifically, the permission message requests the authentication node 3 to generate the data block 10 with viewing permission and the necessary information included in the permission message is information to be used to generate the data block 10 with viewing permission. The permission message includes a set of information shown in FIG. 15. As compared with FIG. 14, the set of information in FIG. 15 includes the same information as in FIG. 14 (in other words, information included in the request message from the request node 2*a*) but has the dual signature of the patient and the generation node 2*b* replacing the dual signature of the patient and the request node 2*a*, and further includes information for identifying the generation node 2*b* (hereafter, generation node ID information). The generation node ID information may be the address of the generation node 2*b* in the viewing procedure management system 1.

Because the set of information shown in FIG. 15 includes the patient address and the examination sequential number of the patient address, the target examination data can be identified based on the set of information. In some embodiments, the set of information may further include examination data ID information (e.g., URL or URN described above) for directly identifying the target examination data. The generation node 2*b* generates the permission message including the above information.

Because the request message transmitted from the request node 2*a* includes various pieces of information shown in FIG. 14, the generation node 2*b* in the present embodiment uses these pieces of information to generate the set of information shown in FIG. 15. In some embodiments, when the dual signature in the request message is successfully authenticated (Yes in STEP 71 in FIG. 11), the generation node 2*b* may examine and obtain these pieces of information shown in FIG. 14. In this case, the request message may include information that is difficult to obtain for the generation node 2*b* (e.g., the patient address, the examination sequential number, or the dual signature of the target patient and the generation node 2*b*).

After generating the permission message, the generation node 2*b* transmits the permission message to the authentication node 3 in the viewing procedure management system 1 (STEP 75 in FIG. 12). After transmission, the generation node 2*b* waits for a predetermined period and confirms that an error message (described later) is not received, and then ends the viewing permission process.

After receiving the permission message transmitted from the generation node 2*b*, the authentication node 3 starts a viewing permission registration process as described below. The received permission message includes the patient's approval message dually signed by the target patient and the generation node 2*b*. The authentication node 3 authenticates the dually signed patient's approval message using the public key of the target patient and the public key of the generation node 2*b* in the same manner as in the authentication by the generation node 2*b* in STEP 70 (STEP 80). The authentication node 3 then determines whether the patient's approval message is successfully authenticated (STEP 81). When the patient's approval message is not successfully authenticated (No in STEP 81), the authentication node 3 transmits an error message indicating that the authentication is not successful to the generation node 2*b* (STEP 82), and ends the viewing permission registration process.

Figure 16:
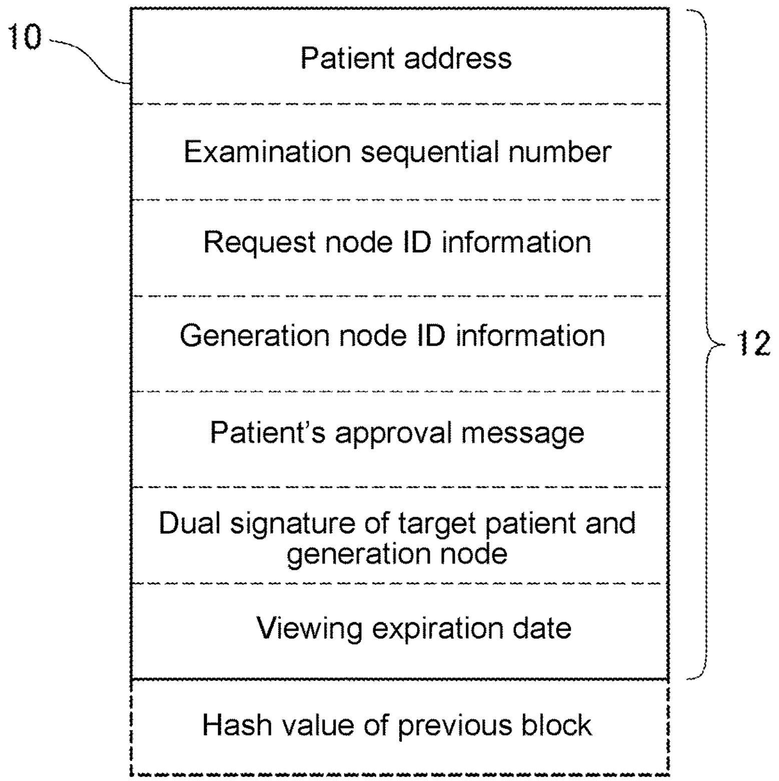
FIG. 16 is a diagram describing a data block 10 with viewing permission generated by the authentication node 3.

In contrast, when the patient's approval message is successfully authenticated (Yes in STEP 81), the authentication node 3 determines that viewing of the patient examination data by the request node 2*a* is with the consent of the target patient and the generation node 2*b*. Thus, the authentication node 3 generates the data block 10 with viewing permission (STEP 83). The data block 10 with viewing permission herein refers to a data block that provides viewing permission to the request node 2*a*. FIG. 16 is a diagram describing the data block 10 with viewing permission generated by the authentication node 3. As compared with the data (the information included in the request message) shown in FIG. 15, the data block 10 with viewing permission in FIG. 16 includes the set of data included in the request message (hereafter, a data set 12) and further includes the hash value of the previous data block 10.

After generating the data block 10 with viewing permission, the authentication node 3 determines whether to use the generated data block 10 with viewing permission or to use the data block 10 with viewing permission having the highest match with the other data blocks based on the data blocks generated by the other authentication nodes 3. The authentication node 3 then transmits the determined data block 10 with viewing permission to all the patient examination nodes 2 (STEP 84). Thus, the data block 10 with viewing permission is stored into the patient examination nodes 2 in the blockchain format. When transmitted in STEP 84, the data block 10 with viewing permission is also stored into the authentication nodes 3. After transmitting and storing the data block 10 with viewing permission (STEP 84), the authentication node 3 transmits a viewing password to the request node 2*a* and the generation node 2*b* (STEP 85) and ends the viewing permission registration process.

After receiving the viewing password, the request node 2*a* presents the viewing password to the generation node 2*b* to view the target examination data. The request node 2*a* and the generation node 2*b* can each refer to the data block 10 with viewing permission stored in the blockchain format and confirm the approval from the target patient and the permission from the generation node 2*b*. Thus, the request node 2*a* can request the patient examination data through the generation node 2*b* without concerns for legal risk, and the generation node 2*b* can provide the patient examination data to the request node 2*a* without concerns for legal risk.

Additionally, the data block 10 with viewing permission is stored in all the patient examination nodes 2 and all the authentication nodes 3 included in the viewing procedure management system 1 in the blockchain format and basically cannot be altered later. Thus, the request node 2*a* can reliably prove, later, its viewing with the consent of the target patient and the generation node 2*b*. The generation node 2*b* can reliably prove, later, that it has provided the examination data with approval from the target patient. This can avoid being involved in an unexpected legal action, allowing the examination data stored in the data server 4 for each patient examination node 2 to be effectively used by the other patient examination nodes 2. To obtain such advantageous effects, the request node 2*a* simply requests viewing of the patient examination data through the viewing procedure management system 1, and the generation node 2*b* simply permits the request through the viewing procedure management system 1. This does not increase the burden on the request node 2*a* and the generation node 2*b*.

F. Modifications

The above embodiment may be modified variously. Such modifications are briefly described below focusing on the differences from the embodiment.

F-1. First Modification

In the above embodiment, the request message generated by the request node 2*a* includes the dual signature of the target patient and the request node 2*a* (refer to FIG. 14). The permission message generated by the generation node 2*b* includes the dual signature of the target patient and the generation node 2*b* (refer to FIG. 15). However, for the request message in FIG. 14, it is sufficient when the target patient and the request node 2*a* are signed, and for the permission message in FIG. 15, it is sufficient when the target patient and the generation node 2*b* are signed. Thus, for example, the method for signing the request message and the permission message may be modified.

Figure 17:
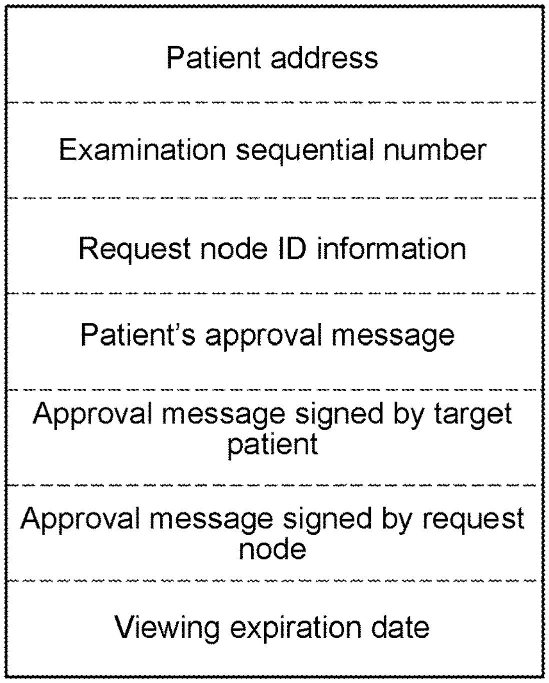
FIG. 17 is a diagram describing an example request message in a first modification.

For example, the request message may not include the dual signature of the target patient and the request node 2*a* shown in FIG. 14 and may include, as shown in FIG. 17, a patient's approval message signed by the target patient and a patient's approval message signed by the request node 2*a*. More specifically, the request node 2*a* provides a patient's approval message to be signed to the target patient, and thus can sign another patient's approval message without the signature of the target patient to generate the patient's message signed by the request node 2*a*. Thus, as shown in FIG. 17, the request node 2*a* may generate the request message including the patient's approval message signed by the target patient and the patient's approval message signed by the request node 2*a*.

Figure 18:
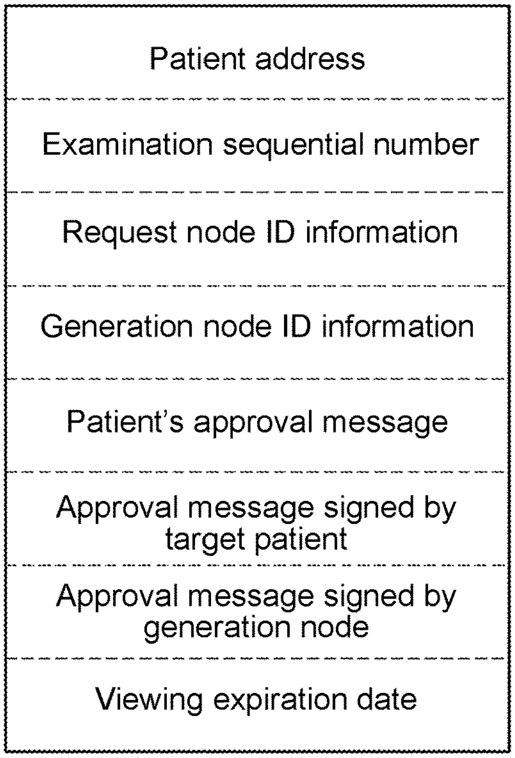
FIG. 18 is a diagram describing an example permission message in the first modification.

The permission message may not include the dual signature of the target patient and the generation node 2*b* shown in FIG. 15 and may include, as shown in FIG. 18, a patient's approval message signed by the target patient and a patient's approval message signed by the generation node 2*b*. More specifically, the generation node 2*b* obtains a patient's approval message without the signature of the target patient (refer to FIG. 14), and uses the message to authenticate the signature of the target patient and the signature of the request node 2*a* included in the request message. Thus, the generation node 2*b* can sign the patient's approval message without the signature of the target patient to generate the patient's approval message signed by the generation node 2*b*. As shown in FIG. 18, the generation node 2*b* may generate the permission message including the patient's approval message received from and signed by the target patient and the patient's approval message signed by the generation node 2*b*.

Further, other methods for signing may be used in place of the method using the public key and the private key described above. For example, a known method for dually signing on an elliptic curve using the private key of the patient and the private key of the generation node 2*b* (Elliptic Curve Digital Signature Algorithm) may be used.

F-2. Second Modification

In the above embodiment and the first modification, the request message generated by the request node 2*a* includes the signature(s) of the target patient and the request node 2*a* (for example, the signed patient's approval message(s)). Similarly, the permission message generated by the generation node 2*b* includes the signature(s) of the target patient and the generation node 2*b* (for example, the signed patient's approval message(s)). In some embodiments, the request message or the permission message may not include signatures.

Figure 19:
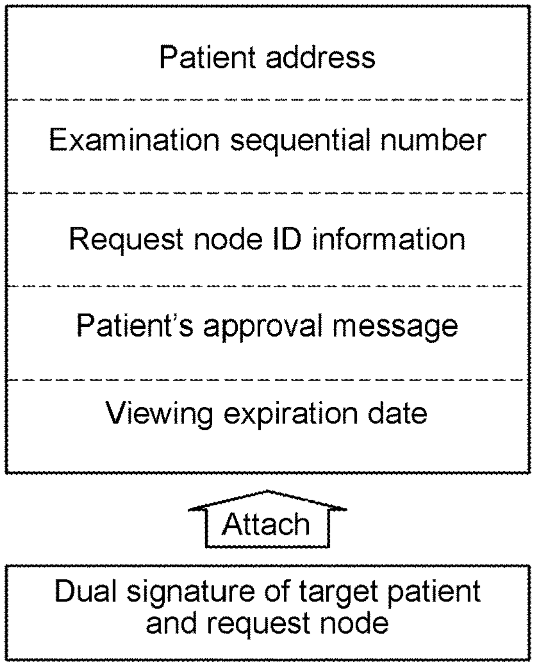
FIG. 19 is a diagram describing a request message in a second modification, with signatures of the patient and the request node 2*a* being attached.

For example, the request message may not include the signatures of the target patient and the request node 2*a*. As shown in FIG. 19, the request node 2*a* may attach the dual signature of the target patient and the request node 2*a* (in this figure, a dually signed patient's approval message) to the request message without signatures. In some embodiments, the request node 2*a* may attach, in place of a dual signature of the target patient and the request node 2*a*, a signature of the target patient (for example, a signed patient's approval message) and a signature of the request node 2*a* (for example, a signed patient's approval message) to the request message without signatures and transmit the message.

Figure 20:
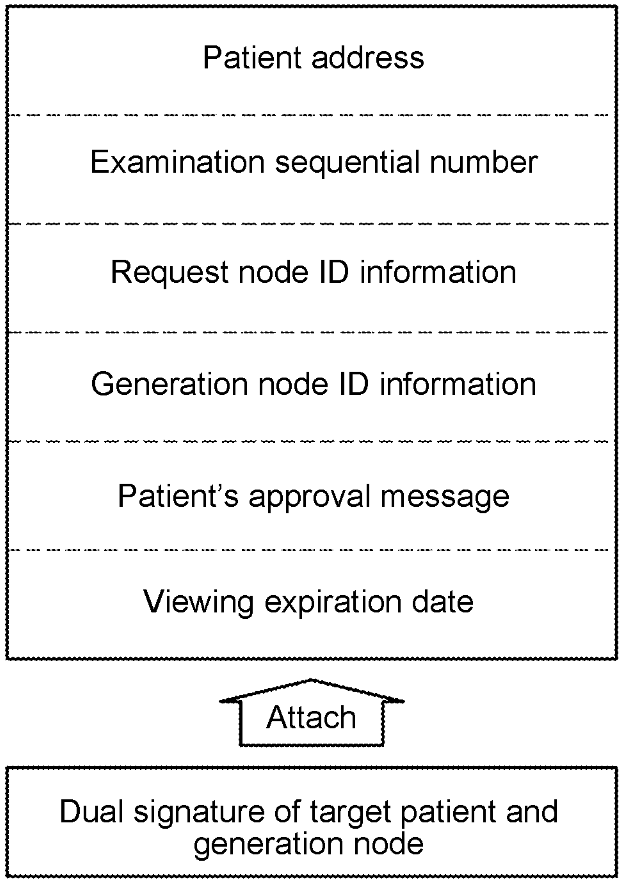
FIG. 20 is a diagram describing a permission message in the second modification, with signatures of the patient and the generation node 2*b* being attached.

For example, the permission message may not include the signatures of the target patient and the generation node 2*b*. As shown in FIG. 20, the generation node 2*b* may attach the dual signature of the target patient and the generation node 2*b* (for example, a dually signed patient's approval message) to the permission message without signatures and transmit the permission message to the authentication node 3. In some embodiments, the generation node 2*b* may attach, in place of a dual signature of the target patient and the generation node 2*b*, a signature of the target patient (for example, a signed patient's approval message) and a signature of the generation node 2*b* (for example, a signed patient's approval message) to the permission message without signatures and transmit the message.

The viewing procedure management system 1 according to the present embodiment and the modifications has been described. However, the present invention is not limited to the above embodiment and modifications and may be implemented in various manners without departing from the spirit and scope of the invention.

REFERENCE SIGNS LIST

1 viewing procedure management system
2 patient examination node
2*a* request node
2*b* generation node
3 authentication node
4 data server
5 communication line
6 patient terminal
10 data block
11 data set
12 data set
20 examination data generator
21 examination data output unit
22 message receiver
23 signature authenticator
24 message generator
25 identification information obtainer
26 message transmitter
27 data block receiver
28 data block storage
30 message receiver
31 signature authenticator
32 data block generator
33 identification information obtainer
34 data block transmitter
35 data block storage

The invention claimed is:

1. A viewing procedure management system for managing a procedure for patient examination data to be viewable by a plurality of patient examination nodes as hardware, the system comprising:

the plurality of patient examination nodes each configured to generate patient examination data based on an examination of a patient and store a plurality of data blocks in a blockchain format; and an authentication node as hardware configured to generate the plurality of data blocks to be stored into the plurality of patient examination nodes, the plurality of patient examination nodes and the authentication node being connected through a communication line, each of the plurality of patient examination nodes including a data block storage configured to store the plurality of data blocks in the blockchain format, and an examination data output unit configured to output the generated patient examination data to a database connected to the patient examination node, the database being separate from a network forming the blockchain and configured to store the patient examination data, wherein the data blocks in the blockchain format are configured to store identification information of the patient examination data while the patient examination data is maintained in the database separate from the data blocks, the plurality of patient examination nodes including a patient examination node being a request node as hardware configured to request viewing of the patient examination data generated by another patient examination node of the plurality of patient examination nodes and a patient examination node being a generation node as hardware configured to generate target examination data being the patient examination data requested by the request node for viewing, the request node including a request message transmitter configured to generate and transmit a request message requesting viewing of the target examination data to the generation node, the request message being a message including predetermined signature data with a signature of a target patient relating to the target examination data or a message to which the signature data with the signature of the target patient relating to the target examination data is attached, the generation node including a patient signature authenticator configured to authenticate, when receiving the request message, the signature of the target patient relating to the signature data received together with the request message, an identification information obtainer configured to obtain, when the signature of the target patient is authenticated, examination data identification information identifying the target examination data and request node identification information identifying the request node, a permission message generator configured to generate a permission message requesting setting of a viewing right for the request node to view the target examination data, the permission message including the examination data identification information and the request node identification information, the permission message being a message including the signature data with the signature of the target patient and signature data with a signature of the generation node or a message to which the signature data with the signature of the target patient and the signature data with the signature of the generation node are attached, and a permission message transmitter configured to transmit the permission message to the authentication node, the authentication node including a permission message authenticator configured to authenticate the signature of the generation node included in or attached to the permission message, a data block generator configured to generate a data block only after the signature of the generation node is authenticated upon receiving the permission message, the data block including no patient examination data and including the request node identification information, the examination data identification information, the signature of the target patient and the signature of the generation node as evidence of granting the viewing right of the target examination data to the request node, and a data block transmitter configured to transmit the generated data block to the plurality of patient examination nodes.

2. The viewing procedure management system according to claim 1, wherein the permission message includes the signature data with the signature of the target patient and the signature data with the signature of the generation node, and the signature data with the signature of the target patient and the signature data with the signature of the generation node are included in a single piece of signature data.

3. The viewing procedure management system according to claim 1, wherein the permission message is a message to which the signature data with the signature of the target patient and the signature data with the signature of the generation node are attached, and the signature data with the signature of the target patient and the signature data with the signature of the generation node are included in a single piece of signature data.

4. The viewing procedure management system according to claim 1, wherein the data block generator in the authentication node generates a data block including a viewing expiration date of the target examination data.

5. The viewing procedure management system according to claim 4, wherein the request message transmitter in the request node transmits the request message including the viewing expiration date obtained from the target patient, the permission message generator in the generation node generates the permission message including the viewing expiration date, and the data block generator in the authentication node generates the data block using the viewing expiration date read from the permission message.

6. A viewing procedure management method for managing a procedure for patient examination data to be viewable by a plurality of patient examination nodes as hardware, the method being implementable with the plurality of patient examination nodes each to generate patient examination data based on an examination of a patient and store a plurality of data blocks in a blockchain format and with an authentication node as hardware to generate the plurality of data blocks to be output to the plurality of patient examination nodes, the plurality of patient examination nodes and the authentication node being connected through a communication line to communicate with one another with a network, the method comprising:

generating and transmitting, with a request node as hardware being a patient examination node of the plurality of patient examination nodes requesting viewing of the patient examination data generated by another patient examination node of the plurality of patient examination nodes, a request message to a generation node being a patient examination node as hardware of the plurality of patient examination nodes generating target examination data being the patient examination data requested by the request node for viewing, the request message requesting viewing of the target examination data, the request message being a message including predetermined signature data with a signature of a target patient relating to the target examination data or a message to which the signature data with the signature of the target patient relating to the target examination data is attached;

authenticating, with the generation node, the signature of the target patient relating to the signature data received together with the request message;

obtaining, with the generation node, when the signature of the target patient is authenticated, examination data identification information identifying the target examination data and request node identification information identifying the request node;

generating, with the generation node, a permission message requesting setting of a viewing right for the request node to view the target examination data and transmitting, with the generation node, the permission message to the authentication node, the permission message including the examination data identification information and the request node identification information, the permission message being a message including the signature data with the signature of the target patient and signature data with a signature of the generation node or a message to which the signature data with the signature of the target patient and the signature data with the signature of the generation node are attached;

authenticating, with the authentication node, the signature of the generation node included in or attached to the permission message; and generating, with the authentication node, only after the signature of the generation node is authenticated upon receiving the permission message, a data block and transmitting, with the authentication node, the data block to the plurality of patient examination nodes, the data block including no patient examination data and including the request node identification information, the examination data identification information, the signature of the target patient, and the signature of the generation node as evidence of granting the viewing right of the target examination data to the request node, wherein the patient examination data is stored in a database separate a network forming from the blockchain, and the data blocks in the blockchain format are configured to store identification information of the patient examination data while the patient examination data is maintained in the database separate from the data blocks.

* * * * *